(12) United States Patent
Zhang et al.

(10) Patent No.: US 7,098,014 B2
(45) Date of Patent: Aug. 29, 2006

(54) *RALSTONIA* AHL-ACYLASE GENE

(76) Inventors: Lian Hui Zhang, 360 Pasir Panjang Road, #03-11, Goldcast Condominium, Singapore (SG) 118699; Jin Ling Xu, 360 Pasir Panjang Road, #03-11, Gold Condominium, Singapore (SG) 118699; Yi Han Lin, 360 Pasir Panjang Road, #04-10, Goldcast Condominium, Singapore (SG) 118699

(*) Notice: Subject to any disclaimer, the term of this patent is extended or adjusted under 35 U.S.C. 154(b) by 0 days.

(21) Appl. No.: 10/502,351

(22) PCT Filed: Jan. 23, 2002

(86) PCT No.: PCT/SG02/00011

§ 371 (c)(1),
(2), (4) Date: Feb. 28, 2005

(87) PCT Pub. No.: WO03/068951

PCT Pub. Date: Aug. 21, 2003

(65) Prior Publication Data

US 2005/0155088 A1    Jul. 14, 2005

(51) Int. Cl.
*C12N 9/14* (2006.01)
(52) U.S. Cl. .................................... 435/195
(58) Field of Classification Search ................ 435/195; 536/23.2
See application file for complete search history.

(56) References Cited

FOREIGN PATENT DOCUMENTS

WO    WO 01/98214 A1    12/2001

OTHER PUBLICATIONS

Allison et al., "Extracellular products as mediators of the formation and detachment of *Pseudomonas fluorescens* biofilms," FEMS Microbiol. Lett. 167:179-184, 1998.
Bassler, et al., "Cross-species induction of luminescence in the quorum-sensing bacterium *Vibrio harveyi*," *J. Bacteriol.* 179:4043-4045, 1997.
Beck von Bodman et al., "Capsular polysaccharide biosynthesis and pathogenicity in *Erwinia stewartii* require induction by an N-acyl homoserine lactone autoinducer," *J. Bacteriol.* 177:5000-5008, 1995.
Cao et al., "Purification and structural identification of an autoinducer for the luminescence system of *Vibrio harveyi*," *J. Biol. Chem.* 264:21670-21676, 1989.
Cha et al., "Production of acyl-homoserine lactone quorum-sensing signals by gram-negative plant-associated bacteria," *Mol. Plant Microbe Interact.* 11:1119-1129, 1998.
Costa et al., "EcbI and EcbR: homologs of LuxI and LuxR affecting antibiotic and exoenzyme production by *Erwinia carotovora* subsp. *Betavasculorum*," *Can. J. Microbiol.* 43:1164-1171, 1997.
Daumy et al., "Role of protein subunits in Proteus rettgeri penicillin G acylase," *J. Bacteriol.* 163:1279-1287, 1985.

Davies et al., "The involvement of cell-to-cell signals in the development of a bacterial biofilm," *Science* 280:295-298, 1998.
Dong et al., "AiiA, an enzyme that inactivates the acyl homoserine lactone quorum-sensing signal and attenuates the virulence of *Erwinia carotovora*," *Proc. Natl. Acad. Sci. USA* 97:3526-3531, 2000.
Dong et al., "Quenching quorum sensing-dependent bacterial infection by an N-acyl homoserine lactonase," *Nature* 411:813-817, 2001.
Dumenyo et al., "Genetic and physiological evidence for the production of N-acyl homoserine lactones by *Pseudomonas syringae* pv. *syringae* and other fluorescent plant pathogenic *Pseudomonas* species," *Eur. J. Plant Pathol.* 104:569-582, 1998.
Dunphy et al., A homoserine lactone autoinducer regulates virulence of an insect-pathogenic bacterium, *Xenorhabdus nematophilus* (Enterobacteriaceae), *J. Bacteroil.* 179:5288-5291, 1997.
Eberhard et al., "Structural identification of autoinducer of *Photobacterum fischeri luciferase*," Biochemistry 20:2444-2449, 1981.
Eberl et al., "Involvement of N-acyl-L-homoserine lactone autoinducers in controlling the multicellular behaviour of *Serratia liquefaciens*," Mol. Microbiol. 20:127-136, 1996.
Fuqua et al., "Conserved cis-acting promoter elements are required for density-dependent transcription of *Agrobacterium tumefaciens* conjugal transfer genes," *J. Bacteriol.* 178:435-440, 1996.
Inokoshi et al., "Cloning and sequencing of the aculeacin A acylasae-encoding gene from *Actinoplanes utahensis* and expression in Streptomyces lividans," Gene 119:29-35, 1992.
Jones et al., "The Lux autoinducer regulates the production of exoenzyme virulence determinants in *Erwinia carotovora* and *Pseudomonas aeruginosa*," EMBO J. 12:2477-2482, 1993.
Leadbetter et al., "Metabolism of acyl-homoserine lactone quorum sensing signals by *Variovorax paradoxus*," *J. Bacterioll.* 182:6921-6926, 2000.
Leadbetter, J.R., "Quieting the raucous crowd," *Nature* 411:748-749, 2001.
Lewenza et al., "Quorum sensing in *Burkholderia cepacia*: identification of the LuxRI homologs CepRI," *J. Bacteriol.* 181:748-756, 1999.
Matsuda et al., "Molecular cloning and structure of the gene for 7β-(4-carboxybutanamido) cephalosporadic acid acylase from a *Pseudomonas strain*," *J. Bacteriol.* 163:1222-1228, 1985.

(Continued)

*Primary Examiner*—Rebecca E. Prouty
*Assistant Examiner*—Iqbal Chowdhury
(74) *Attorney, Agent, or Firm*—Rothwell, Figg, Ernst & Manbeck pc

(57) ABSTRACT

This invention provides a gene, qsbA, which encodes a protein useful for inactivating certain bacterial quorum-sensing signal molecules (N-acyl homoserine lactones) which participate in bacterial virulence and biofilm differentiation pathways. This gene was isolated from *Ralstonia* sp., strain XJ12B. The invention also provides the QsbA protein, which possesses N-acyl homoserine lactone inactivating activity.

6 Claims, 2 Drawing Sheets

OTHER PUBLICATIONS

Matsuda et al., "Nucleotide sequence of the genes for two distinct cephalosporin acylases from a *Pseudomonas strain,* " *J. Bacteriol.* 169:5821-5826, 1987.

Nasser et al., "Characterization of the *Erwinia chrysanthemi* expI-expR locus directing the syntehsis of two N-acyl-homoserine lactone signal molecules," *Mol. Microbiol.* 29:1391-1405, 1998.

Passador et al., "Expression of *Pseudomonas aeruginosa* virulence genes requires cell-to-cell communication," *Science* 260:1127-1130, 1993.

Pearson et al., "Structure of the autoinducer required for expression of *Pseudomonas aeruginosa* virulence genes," Proc. Natl. Acad. Sci. USA 91:197-201, 1994.

Piper et al., "Conjugation factor of *Agrobacterium tumefaciens* regulates Ti plasmid transfer by autoinduction," *Nature* 362:448-450, 1993.

Pirhonen et al., "A small diffusible signal molecule is responsible for the global control of virulence and exoenzyme production in the plant pathogen *Erwinia carotovora,* " *EMBO J.* 12:2467-2476, 1993.

Schumacher et al., "Penicillin acylase from *E. Coli* unique gene-protein relation," *Nucleic Acids Res.* 14:5713-5727, 1986.

Staskawicz et al., "Molecular characterization of cloned avirulence genes from race 0 and race 1 of *Pseudomonas syringae* pv. *Glycinea,*" *J. Bacteriol.* 169:5789-5794, 1987.

Takeshima et al., "A deacylation enzyme for aculeacin A, a neutral lipopeptide antibiotic, from *Actinoplanes utahensis*: purification and characterization," *J. Biochem.* 105:606-610, 1989.

Verhaert et al., "Molecular cloning and analysis of the gene encoding the thermostable penicillin G acylase from *Alcaligenes faecalis,*" *App. Env. Microbiol.* 63:3412-3418, 1997.

White et al., "Genome Sequence of the Radioresistant Bacterium Deinococcus Radiodurans R1," *Science* 286:1571-1577, 1999.

Zhang et al., "Agrobacterium conjugation and gene regulation by N-acyl-L-homoserine lactones," *Nature* 362:446-448, 1993.

Swiss-Prot. Accession Q9RYQ4, White et al., (two pages) (1999).

Embl Accession AE001836, White et al., (ninety pages) (1999).

SEQUENCE LISTING

<160> NUMBER OF SEQ ID NOS: 7

<210> SEQ ID NO 1
<211> LENGTH: 3743
<212> TYPE: DNA
<213> ORGANISM: Ralstonia sp.
<220> FEATURE:
<221> NAME/KEY: misc_feature
<222> LOCATION: (16)..(16)
<223> OTHER INFORMATION: n is a, c, g, or t

<400> SEQUENCE: 1

```
gtttgggaaa gtgggnagcg cgctgtgcag cgccccgccc ctcagccgcg cagctcggcg      60
cgcaccgaat gcgcgcgccg gtgggcgccc ggcggctggc cggtgtggcg ccggatcagg     120
cgccggaagg cggacatgtc gtgataaccg cactgttcgg cgattgccgt caggctcagc     180
gtgctgactt ccagcaggtg gcaggcgcgc tccacgcgca gccggtgcag caattgcagc     240
ggcgaggtgc ccagggtctt ggtgaaatgc cgcagcagcg tgcgctcgct ggtcgaggcg     300
gcggcggcca gcttggccag gtcgaacggc tcgtgcaggt gctgctgcag gtagcgccgc     360
gcccgcagta ccacgctggt gcggatggcg ggcttgctgc gcagccagat ggcggtggac     420
tcaccgcgcg acgggtggtc gagcacggcc tggccgaggg tgcgtgccag ccgggtgtcg     480
gccaggcggc cgaccaggcg ctgcgtgagc gccacgccgt gctccatcgc gcgcgccgtc     540
agcacgttgc cgctgctgac gatggcctgc tccgccacca ccttcagctg cgggtagttg     600
```

-continued

```
ccgtgcagcc agccggcgat cagccacgtc accgtcaagc gccggccggc gggcagcgcg    660
ccggccagca gcgccacgcc ggtgaaggac gaggccacca gcctgccgg cgtccaggta    720
gcgccggatg gtggcgcgtt cccactccag cagggccagg cgctgctcca gcgtgctgat    780
gtggtcgaaa tgcaggggcg ggacgaccag cgcgtcgccc agcgcggcgt cgcccgccgg    840
cagcggctgg cagcggcagg ccaggtctc ggcggcggcc tgccagcggg ccgggtcgcg    900
cgcgaccagc cgccacccga acaccgggct ggcggcatcg gcacgcttgc cggcatgcat    960
ggaggcgagc gcattggcca cgccgagggt gtcggcgacg tcgccagcg tggagaggcc   1020
ggcgtcggga aggtcagca ggtcgatgtc ggcatccgca agtataggg gaggcgggcg   1080
gaggcctcct gcgtggcggg attgacccca actctggcgg gaatacctct ttcctccggg   1140
cgggccccag tcgacgatac ggcggtggct gcgcctgcgc gccgccgcaa gactagagcg   1200
acacaagaca agaccgacaa caggagacaa cgcatgatgc agggattcgc gctgcgcggc   1260
acgctcgcca tggccgcgct cgcggcgctg gccggctgcg ccagttccac cgatggccgc   1320
tgggggtcgc tcagcgacac cggcctgtcc gccgagatcc gccgcaccgg cttcggcatt   1380
ccgcacatcc gcgccaacga ctacgccagc ctcggctatg gcatggccta tgcctacgcg   1440
caggacaacc tgtgcctgct ggccgaccag gtggtcaccg tcaacggcga gcgctcgaag   1500
accttcgggc ccgagggcac cgtgacggtc tcgttcaagc cgatccccaa cctgcagtcg   1560
gacgccttct tcaagggcat cttcgacgag gacggcctgc gcgccggtta tgcgcagatg   1620
tcgcccgagg cgcgcgagct gctgcgcggc tacatcgccg gcttcaaccg ctatctcaag   1680
gacacgccgc ccgccaactt cccggccgcc tgccgcaatg ccgcctgggt gcgtccgctc   1740
acgctgggcg acatgatgcg catgggcgaa gagaaggcga tccaggccag cgccggcgcc   1800
atgctggcgg gcatcgtcgc cgcgcagccg ccgggccgca cgccggtggc cgagcgcgag   1860
attccgccgc aggccgtcga caccgtggcg ctggaccgcg aactgcagct gcgcgacatg   1920
ccgatcggct ccaacggctg ggccttcggc gctgacgcca ccgccaaccg gcgcggcgtg   1980
ctgctcggca atccgcactt cccgtggacg accaccaacc gcttctacca ggtccacctg   2040
acggtgcccg gcaagctcga cgtgatgggc gcctcgatcg cggccttccc ggtggtgagc   2100
atcggcttca acaaggacgt ggcgtggacg cacaccgtct ccaccggccg ccgcttcacc   2160
ttgttcgaac tgaagctggc cgaaggcgac ccgaccacct acctggtcga cggcacgccg   2220
cacaagatga ccacccgcac ggtcgccttc gacgtcaagc tgccggacgg ccgcctcgag   2280
cgccgcacgc acaccttcta cgacaccatc tacggcccgg tgctgtcgat gccgagcggc   2340
ggcatgccgt ggaccacgca gaaggcctac gccctgcgcg acgccaaccg caacaacacg   2400
cgctcggtcg acagctggct gcatatcggg caggcccggg acgtggccgg catccgccag   2460
gccatcggca acctgggcat tccctgggtc aacaccatcg ccaccgaccg caacggccgc   2520
gcgctgttcg ccgacgtgtc gaccacgccg gacgtgccgg ccgcggagct ccagcgctgt   2580
gccccgtcgc cgctggccgg caaactcttc aaggacgcgg gcctggtgct gctcgacggc   2640
tcgcgcggca cctgcaactg gcaggtcgat ccggcttcgc cggtacccgg gctggtggcg   2700
cccgcgcgca tgccggtgct cgagcgcgac gactacgtcg ccaacagcaa tgacagctcc   2760
tggctgacca accccgcgca aaagctgacc ggcttctcgc cggtgatggg ctcggtcgac   2820
gtaccgcagc ggctgcgcac gcgcatcggc ctgatcgaga tcggccgccg cctggccggc   2880
accgacggac tgcccggcaa ccgcatcgat ctgccgaacc tgcaggcgat gatcttcagc   2940
```

-continued

```
aatgccaacc tggcgggaca actggtgctg ggcgacctgc tcgcggcatg caaggccacg    3000
ccggccccgg atgccgacgt gcgcgacggc tgcgccgccc tcggccagtg gaaccgcacc    3060
agcaacgccg acgcccgcgc cgcgcacctg ttccgcgagt tctggatgcg cgccaaggac    3120
atcgcgcagg tgcacgccgt cgagttcgac ccggccgacc cggtccacac gccgcgcggc    3180
ctgcgcatga cgacgcgac ggtacgcacg gcggtgttca aggcgctgaa ggaagccgtg    3240
ggcgcggtgc gcaaggcggg cttcgcgctg gatgcgccgc tgggcacggt acaggccgcg    3300
cacgcaccgg acggctccat cgccctgcac ggcggcgagg aatacgaagg cgtgctcaac    3360
aagctgcaaa ccctgccgat cgggccgaag gggctgccgg tgtatttcgg caccagctac    3420
atccagaccg tgaccttcga cgaccagggc ccggtcgccg acgccatcct cacctacggc    3480
gaatcgaccg accacgcctc gccgcacgcg ttcgaccaga tgcgtgcgta ctcgggcaag    3540
cactggaacc ggctgccgtt ctccgaagcg gccatcgcgg ccgatccggc gctgaaggtg    3600
atgcggttgt cgcagtgagg gctgccggtg cctggaaaaa cgccccgctt gtgcggggcg    3660
ttttttttgcc agtgtgaatg gctcaatcgt gttggaaacc gcatccggac atgactgtat    3720
tgtgactctg cctgtgtccg tgt                                            3743
```

<210> SEQ ID NO 2
<211> LENGTH: 794
<212> TYPE: PRT
<213> ORGANISM: Ralstonia sp.

<400> SEQUENCE: 2

```
Met Met Gln Gly Phe Ala Leu Arg Gly Thr Leu Ala Met Ala Ala Leu
 1               5                  10                  15

Ala Ala Leu Ala Gly Cys Ala Ser Ser Thr Asp Gly Arg Trp Gly Ser
             20                  25                  30

Leu Ser Asp Thr Gly Leu Ser Ala Glu Ile Arg Arg Thr Gly Phe Gly
         35                  40                  45

Ile Pro His Ile Arg Ala Asn Asp Tyr Ala Ser Leu Gly Tyr Gly Met
     50                  55                  60

Ala Tyr Ala Tyr Ala Gln Asp Asn Leu Cys Leu Leu Ala Asp Gln Val
 65                  70                  75                  80

Val Thr Val Asn Gly Glu Arg Ser Lys Thr Phe Gly Pro Glu Gly Thr
                 85                  90                  95

Val Thr Val Ser Phe Lys Pro Ile Pro Asn Leu Gln Ser Asp Ala Phe
            100                 105                 110

Phe Lys Gly Ile Phe Asp Glu Asp Gly Leu Arg Ala Gly Tyr Ala Gln
        115                 120                 125

Met Ser Pro Glu Ala Arg Glu Leu Leu Arg Gly Tyr Ile Ala Gly Phe
    130                 135                 140

Asn Arg Tyr Leu Lys Asp Thr Pro Ala Asn Phe Pro Ala Ala Cys
145                 150                 155                 160

Arg Asn Ala Ala Trp Val Arg Pro Leu Thr Leu Gly Asp Met Met Arg
                165                 170                 175

Met Gly Glu Glu Lys Ala Ile Gln Ala Ser Ala Gly Ala Met Leu Ala
            180                 185                 190

Gly Ile Val Ala Ala Gln Pro Pro Gly Arg Thr Pro Val Ala Glu Arg
        195                 200                 205

Glu Ile Pro Pro Gln Ala Val Asp Thr Val Ala Leu Asp Arg Glu Leu
    210                 215                 220

Gln Leu Arg Asp Met Pro Ile Gly Ser Asn Gly Trp Ala Phe Gly Ala
```

-continued

```
            225                 230                 235                 240
Asp Ala Thr Ala Asn Arg Arg Gly Val Leu Leu Gly Asn Pro His Phe
                    245                 250                 255
Pro Trp Thr Thr Thr Asn Arg Phe Tyr Gln Val His Leu Thr Val Pro
                260                 265                 270
Gly Lys Leu Asp Val Met Gly Ala Ser Ile Ala Ala Phe Pro Val Val
                275                 280                 285
Ser Ile Gly Phe Asn Lys Asp Val Ala Trp Thr His Thr Val Ser Thr
            290                 295                 300
Gly Arg Arg Phe Thr Leu Phe Glu Leu Lys Leu Ala Glu Gly Asp Pro
305                 310                 315                 320
Thr Thr Tyr Leu Val Asp Gly Thr Pro His Lys Met Thr Thr Arg Thr
                325                 330                 335
Val Ala Phe Asp Val Lys Leu Pro Asp Gly Arg Leu Glu Arg Arg Thr
                340                 345                 350
His Thr Phe Tyr Asp Thr Ile Tyr Gly Pro Val Leu Ser Met Pro Ser
                355                 360                 365
Gly Gly Met Pro Trp Thr Thr Gln Lys Ala Tyr Ala Leu Arg Asp Ala
            370                 375                 380
Asn Arg Asn Thr Arg Ser Val Asp Ser Trp Leu His Ile Gly Gln
385                 390                 395                 400
Ala Arg Asp Val Ala Gly Ile Arg Gln Ala Ile Gly Asn Leu Gly Ile
                405                 410                 415
Pro Trp Val Asn Thr Ile Ala Thr Asp Arg Asn Gly Arg Ala Leu Phe
                420                 425                 430
Ala Asp Val Ser Thr Thr Pro Asp Val Pro Ala Ala Glu Leu Gln Arg
                435                 440                 445
Cys Ala Pro Ser Pro Leu Ala Gly Lys Leu Phe Lys Asp Ala Gly Leu
            450                 455                 460
Val Leu Leu Asp Gly Ser Arg Gly Thr Cys Asn Trp Gln Val Asp Pro
465                 470                 475                 480
Ala Ser Pro Val Pro Gly Leu Val Ala Pro Ala Arg Met Pro Val Leu
                485                 490                 495
Glu Arg Asp Asp Tyr Val Ala Asn Ser Asn Asp Ser Ser Trp Leu Thr
                500                 505                 510
Asn Pro Ala Gln Lys Leu Thr Gly Phe Ser Pro Val Met Gly Ser Val
            515                 520                 525
Asp Val Pro Gln Arg Leu Arg Thr Arg Ile Gly Leu Ile Glu Ile Gly
            530                 535                 540
Arg Arg Leu Ala Gly Thr Asp Gly Leu Pro Gly Asn Arg Ile Asp Leu
545                 550                 555                 560
Pro Asn Leu Gln Ala Met Ile Phe Ser Asn Ala Asn Leu Ala Gly Gln
                565                 570                 575
Leu Val Leu Gly Asp Leu Leu Ala Ala Cys Lys Ala Thr Pro Ala Pro
            580                 585                 590
Asp Ala Asp Val Arg Asp Gly Cys Ala Ala Leu Gly Gln Trp Asn Arg
            595                 600                 605
Thr Ser Asn Ala Asp Ala Arg Ala His Leu Phe Arg Glu Phe Trp
            610                 615                 620
Met Arg Ala Lys Asp Ile Ala Gln Val His Ala Val Glu Phe Asp Pro
625                 630                 635                 640
Ala Asp Pro Val His Thr Pro Arg Gly Leu Arg Met Asn Asp Ala Thr
                645                 650                 655
```

```
Val Arg Thr Ala Val Phe Lys Ala Leu Lys Glu Ala Val Gly Ala Val
            660                 665                 670

Arg Lys Ala Gly Phe Ala Leu Asp Ala Pro Leu Gly Thr Val Gln Ala
            675                 680                 685

Ala His Ala Pro Asp Gly Ser Ile Ala Leu His Gly Gly Glu Glu Tyr
            690                 695                 700

Glu Gly Val Leu Asn Lys Leu Gln Thr Leu Pro Ile Gly Pro Lys Gly
705                 710                 715                 720

Leu Pro Val Tyr Phe Gly Thr Ser Tyr Ile Gln Thr Val Thr Phe Asp
                725                 730                 735

Asp Gln Gly Pro Val Ala Asp Ala Ile Leu Thr Tyr Gly Glu Ser Thr
            740                 745                 750

Asp His Ala Ser Pro His Ala Phe Asp Gln Met Arg Ala Tyr Ser Gly
            755                 760                 765

Lys His Trp Asn Arg Leu Pro Phe Ser Glu Ala Ala Ile Ala Ala Asp
            770                 775                 780

Pro Ala Leu Lys Val Met Arg Leu Ser Gln
785                 790

<210> SEQ ID NO 3
<211> LENGTH: 785
<212> TYPE: PRT
<213> ORGANISM: Deinococcus radiodurans

<400> SEQUENCE: 3

Met Ser Arg Ser Pro Phe Ser Ser Val Ser Leu Pro Ala Arg Leu Leu
1               5                   10                  15

Leu Gly Ser Leu Leu Gly Pro Leu Met Leu Gly Gly Ala Ala Ser
            20                  25                  30

Ala Gln Thr Tyr Gln Val Gln Ile Gln Arg Thr Ala His Gly Ile Pro
            35                  40                  45

His Ile Gln Ala Ser Asp Leu Gly Gly Ile Gly Tyr Gly Val Gly Tyr
        50                  55                  60

Ser Tyr Ala Gln Asp Asn Leu Cys Leu Leu Ala Asp Gln Val Met Thr
65                  70                  75                  80

Val Arg Gly Glu Arg Ser Lys Phe Leu Gly Ala Glu Gly Lys Thr Val
            85                  90                  95

Val Gly Phe Gln Pro Val Asn Asn Leu Asp Ser Asp Val Phe Phe Lys
            100                 105                 110

Thr Val Ile Glu Pro Gly Arg Leu Gln Ala Gly Tyr Arg Asp Gln Pro
            115                 120                 125

Gln Ile Leu Ala Leu Met Arg Gly Tyr Val Ala Gly Val Asn Arg Tyr
        130                 135                 140

Leu Arg Asp Thr Pro Pro Glu Gln Trp Pro Ser Ala Cys Arg Asn Ala
145                 150                 155                 160

Asp Trp Val Arg Pro Leu Thr Glu Leu Asp Val Met Arg Leu Gly Glu
            165                 170                 175

Glu Lys Ala Ile Gln Ala Ser Ala Gly Ala Met Val Ser Ala Ile Thr
            180                 185                 190

Ser Ala Arg Pro Pro Gln Ala Gly Ala Ser Thr Ala Ala Pro Arg Pro
            195                 200                 205

Asp Leu Ala Ala Phe Asn Arg Gln Tyr Arg Phe Asn Asp Leu Pro Ile
        210                 215                 220

Gly Ser Asn Gly Trp Ala Phe Gly Ser Glu Ala Thr Thr Asn Gly Arg
```

-continued

```
        225                 230                 235                 240
Gly Leu Leu Gly Asn Pro His Phe Pro Trp Glu Thr Ser Asn Arg
                245                 250                 255
Phe Tyr Gln Leu His Leu Thr Leu Pro Gly Gln Phe Asp Val Met Gly
            260                 265                 270
Ala Ser Leu Gly Gly Met Pro Val Val Asn Ile Gly Phe Asn Gln Asp
            275                 280                 285
Val Ala Trp Thr His Thr Val Ser Thr Asp Lys Arg Phe Thr Leu Ala
        290                 295                 300
Ala Leu Thr Leu Val Pro Gly Asp Pro Leu Ser Tyr Val Lys Asp Gly
305                 310                 315                 320
Gln Gln Arg Arg Leu Gln Arg Arg Thr Ala Val Ile Glu Val Lys Thr
                325                 330                 335
Ala Asn Gly Pro Arg Leu His Thr Arg Thr Val Tyr Phe Thr Pro Glu
            340                 345                 350
Gly Pro Leu Val Asn Leu Pro Ala Gly Leu Thr Trp Thr Pro Gln
            355                 360                 365
Tyr Ala Phe Ala Leu Arg Asp Ala Asn Arg Asn Asn Thr Arg Met Leu
        370                 375                 380
Ala Thr Trp Leu Gly Phe Ala Gly Ala Lys Ser Val Arg Asp Ile Arg
385                 390                 395                 400
Ala Ser Leu Asn Val Gln Gly Ile Pro Trp Val Asn Thr Ile Ala Ala
                405                 410                 415
Asp Arg Ala Gly Ser Ala Leu Tyr Ala Asp Ile Ser Ser Pro Asn
            420                 425                 430
Val Ser Ala Ala Gln Gln Ala Cys Thr Pro Pro Leu Ala Pro
        435                 440                 445
Leu Phe Pro Ala Ala Gly Leu Ala Val Leu Asp Gly Ser His Ser Ala
        450                 455                 460
Cys Asp Trp Lys Thr Asp Pro Ala Ser Arg Val Pro Gly Leu Arg Ala
465                 470                 475                 480
Pro Asp Lys Met Pro Val Leu Ile Arg Gln Asp Phe Val Ala Asn Ser
                485                 490                 495
Asn Asn Ser Ala Trp Leu Ala Asn Pro Ala Pro Gln Thr Gly Leu
            500                 505                 510
Asp Pro Leu Val Gly Glu Val Asn Ala Pro Gln Ser Pro Arg Thr Arg
        515                 520                 525
Met Gly Leu Leu Glu Ile Gly Arg Arg Leu Ser Gly Thr Asp Gly Leu
        530                 535                 540
Pro Gly Arg Thr Phe Asp Ile Pro Thr Leu Gln Ala Thr Leu Leu Arg
545                 550                 555                 560
Glu Ser Asn Leu Thr Gly Glu Met Tyr Ala Ala Asp Ala Ala Lys Leu
                565                 570                 575
Cys Gln Ser Ala Gly Gly Ala Glu Leu Gln Pro Ala Cys Asn Ala Leu
            580                 585                 590
Ala Ala Trp Asp Arg Arg Ser Ser Gln Glu Ser Arg Gly Ala Ala Leu
            595                 600                 605
Trp Arg Glu Phe Trp Arg Arg Ala Arg Ala Ile Pro Asn Val Tyr Ala
        610                 615                 620
Val Pro Phe Asp Pro Ala Asp Pro Val Asn Thr Pro Arg Gly Leu Asn
625                 630                 635                 640
Thr Ala Asp Pro Ala Ala Gln Thr Ala Leu Leu Gly Ala Leu Arg Glu
                645                 650                 655
```

```
Ala Ala Ala Ala Leu Thr Ala Ala Gly Ile Pro Phe Asp Ala Pro Leu
            660                 665                 670

Gly Glu Val Gln Gly Val Val Arg Gly Gly Asp Phe Ile Ser Leu Pro
            675                 680                 685

Gly Gly Ala Glu Phe Glu Gly Val Leu Asp Lys Ile Asp Phe Asn Pro
            690                 695                 700

Leu Ala Pro Gly Gly Tyr Arg Gly Val Val Gly Asn Ala Ser Ser Tyr
705                 710                 715                 720

Ile Gln Thr Val Gly Phe Thr Asp Ser Gly Val Gln Ala Glu Ala Val
            725                 730                 735

Leu Thr Tyr Ser Gln Ser Ser Asn Pro Glu Ser Pro Tyr Phe Ser Asp
            740                 745                 750

Gln Thr Arg Leu Phe Ser Arg Ser Glu Trp Val Lys Leu Pro Phe Thr
            755                 760                 765

Gln Pro Glu Ile Glu Ala Asp Pro Thr Arg Thr Val Val Gln Leu Ser
            770                 775                 780

Glu
785

<210> SEQ ID NO 4
<211> LENGTH: 786
<212> TYPE: PRT
<213> ORGANISM: Actinoplanes utahensis

<400> SEQUENCE: 4

Met Thr Ser Ser Tyr Met Arg Leu Lys Ala Ala Ile Ala Phe Gly
1               5                   10                  15

Val Ile Val Ala Thr Ala Ala Val Pro Ser Pro Ala Ser Gly Arg Glu
            20                  25                  30

His Asp Gly Gly Tyr Ala Ala Leu Ile Arg Arg Ala Ser Tyr Gly Val
            35                  40                  45

Pro His Ile Thr Ala Asp Asp Phe Gly Ser Leu Gly Phe Gly Val Gly
        50                  55                  60

Tyr Val Gln Ala Glu Asp Asn Ile Cys Val Ile Ala Glu Ser Val Val
65                  70                  75                  80

Thr Ala Asn Gly Glu Arg Ser Arg Trp Phe Gly Ala Thr Gly Pro Asp
            85                  90                  95

Asp Ala Asp Val Arg Thr Thr Ser Ser Thr Gln Ala Ile Asp Asp Arg
            100                 105                 110

Val Ala Glu Arg Leu Leu Glu Gly Pro Arg Asp Gly Val Arg Ala Pro
            115                 120                 125

Cys Asp Asp Val Arg Asp Gln Met Arg Gly Phe Val Ala Gly Tyr Asn
    130                 135                 140

His Phe Leu Arg Arg Thr Gly Val His Arg Leu Thr Asp Pro Ala Cys
145                 150                 155                 160

Arg Gly Lys Ala Trp Val Arg Pro Leu Ser Glu Ile Asp Leu Trp Arg
                165                 170                 175

Thr Ser Trp Asp Ser Met Val Arg Ala Gly Ser Gly Ala Leu Leu Asp
            180                 185                 190

Gly Ile Val Ala Thr Pro Pro Thr Ala Gly Pro Ala Ser Ala
        195                 200                 205

Pro Glu Ala Pro Asp Ala Ala Ala Ile Ala Ala Leu Asp Gly Thr
    210                 215                 220

Ser Ala Gly Ile Gly Ser Asn Ala Tyr Gly Leu Gly Ala Gln Ala Thr
```

-continued

```
            225                 230                 235                 240
Val Asn Gly Ser Gly Met Val Leu Ala Asn Pro His Phe Pro Trp Gln
                245                 250                 255
Gly Ala Glu Arg Phe Tyr Arg Met His Leu Lys Val Pro Gly Arg Tyr
                260                 265                 270
Asp Val Glu Gly Ala Ala Leu Ile Gly Asp Pro Ile Ile Glu Ile Gly
                275                 280                 285
His Asn Arg Thr Val Ala Trp Ser His Thr Val Ser Thr Ala Arg Arg
                290                 295                 300
Phe Val Trp His Arg Leu Ser Leu Val Pro Gly Asp Pro Thr Ser Tyr
305                 310                 315                 320
Tyr Val Asp Gly Arg Pro Glu Arg Met Arg Ala Arg Thr Val Thr Val
                325                 330                 335
Gln Thr Gly Ser Gly Pro Val Ser Arg Thr Phe His Asp Thr Arg Tyr
                340                 345                 350
Gly Pro Val Ala Val Pro Gly Thr Phe Asp Trp Thr Pro Ala Thr
                355                 360                 365
Ala Tyr Ala Ile Thr Asp Val Asn Ala Gly Asn Asn Arg Ala Phe Asp
                370                 375                 380
Gly Trp Leu Arg Met Gly Gln Ala Lys Asp Val Arg Ala Leu Lys Ala
385                 390                 395                 400
Val Leu Asp Arg His Gln Phe Leu Pro Trp Val Asn Val Ile Ala Ala
                405                 410                 415
Asp Ala Arg Gly Glu Ala Leu Tyr Gly Asp His Ser Val Val Pro Arg
                420                 425                 430
Val Thr Gly Ala Leu Ala Ala Ala Cys Ile Pro Ala Pro Phe Gln Pro
                435                 440                 445
Leu Tyr Ala Ser Ser Gly Gln Ala Val Leu Asp Gly Ser Arg Ser Asp
                450                 455                 460
Cys Ala Leu Gly Ala Asp Pro Asp Ala Ala Val Pro Gly Ile Leu Gly
465                 470                 475                 480
Pro Ala Ser Leu Pro Val Arg Phe Arg Asp Asp Tyr Val Thr Asn Ser
                485                 490                 495
Asn Asp Ser His Trp Leu Ala Ser Pro Ala Ala Pro Leu Glu Gly Phe
                500                 505                 510
Pro Arg Ile Leu Gly Asn Glu Arg Thr Pro Arg Ser Leu Arg Thr Arg
                515                 520                 525
Leu Gly Leu Asp Gln Ile Gln Gln Arg Leu Ala Gly Thr Asp Gly Leu
                530                 535                 540
Pro Gly Lys Gly Phe Thr Thr Ala Arg Leu Trp Gln Val Met Phe Gly
545                 550                 555                 560
Asn Arg Met His Gly Ala Glu Leu Val Arg Asp Asp Leu Val Ala Leu
                565                 570                 575
Cys Arg Arg Gln Pro Thr Ala Thr Ala Ser Asn Gly Ala Ile Val Asp
                580                 585                 590
Leu Thr Ala Ala Cys Thr Ala Leu Ser Arg Phe Asp Glu Arg Ala Asp
                595                 600                 605
Leu Asp Ser Arg Gly Ala His Leu Phe Thr Glu Phe Leu Ala Gly Gly
                610                 615                 620
Ile Arg Phe Ala Asp Thr Phe Glu Val Thr Asp Pro Val Arg Thr Pro
625                 630                 635                 640
Ala Pro Phe Trp Asn Thr Thr Asp Pro Arg Val Arg Thr Ala Leu Ala
                645                 650                 655
```

```
Asp Ala Cys Asn Gly Ser Pro Ala Ser Pro Ser Thr Arg Ser Val Gly
            660                 665                 670

Asp Ile His Thr Asp Ser Arg Gly Glu Arg Ile Pro Ile His Gly
            675                 680                 685

Gly Arg Gly Glu Ala Gly Thr Phe Asn Val Ile Thr Asn Pro Leu Val
            690                 695                 700

Pro Gly Val Gly Tyr Pro Gln Val Val His Gly Thr Ser Phe Val Met
705                 710                 715                 720

Ala Val Glu Leu Gly Pro His Gly Pro Ser Gly Arg Gln Ile Leu Thr
                725                 730                 735

Tyr Ala Gln Ser Thr Asn Pro Asn Ser Pro Trp Tyr Ala Asp Gln Thr
            740                 745                 750

Val Leu Tyr Ser Arg Lys Gly Trp Asp Thr Ile Lys Tyr Thr Glu Ala
            755                 760                 765

Gln Ile Ala Ala Asp Pro Asn Leu Arg Val Tyr Arg Val Ala Gln Arg
            770                 775                 780

Gly Arg
785

<210> SEQ ID NO 5
<211> LENGTH: 777
<212> TYPE: PRT
<213> ORGANISM: Pseudomonas aeruginosa

<400> SEQUENCE: 5

Met Ser Arg Pro Phe Arg Pro Pro Leu Cys Arg Glu Thr Thr Ser Met
1               5                   10                  15

Gly Met Arg Thr Val Leu Thr Gly Leu Ala Gly Met Leu Leu Gly Ser
            20                  25                  30

Met Met Pro Val Gln Ala Asp Met Pro Arg Pro Thr Gly Leu Ala Ala
            35                  40                  45

Asp Ile Arg Trp Thr Ala Tyr Gly Val Pro His Ile Arg Ala Lys Asp
        50                  55                  60

Glu Arg Gly Leu Gly Tyr Gly Ile Gly Tyr Ala Tyr Ala Arg Asp Asn
65                  70                  75                  80

Ala Cys Leu Leu Ala Glu Glu Ile Val Thr Ala Arg Gly Glu Arg Ala
                85                  90                  95

Arg Tyr Phe Gly Ser Glu Gly Lys Ser Ser Ala Glu Leu Asp Asn Leu
            100                 105                 110

Pro Ser Asp Ile Phe Tyr Ala Trp Leu Asn Gln Pro Glu Ala Leu Gln
        115                 120                 125

Ala Phe Trp Gln Ala Gln Thr Pro Ala Val Arg Gln Leu Leu Glu Gly
    130                 135                 140

Tyr Ala Ala Gly Phe Asn Arg Phe Leu Arg Glu Ala Asp Gly Lys Thr
145                 150                 155                 160

Thr Ser Cys Leu Gly Gln Pro Trp Leu Arg Ala Ile Ala Thr Asp Asp
                165                 170                 175

Leu Leu Arg Leu Thr Arg Arg Leu Leu Val Glu Gly Gly Val Gly Gln
            180                 185                 190

Phe Ala Asp Ala Leu Val Ala Ala Pro Gly Ala Glu Lys Val
        195                 200                 205

Ala Leu Ser Gly Glu Gln Ala Phe Gln Val Ala Glu Gln Arg Arg Gln
    210                 215                 220

Arg Phe Arg Leu Glu Arg Gly Ser Asn Ala Ile Ala Val Gly Ser Glu
```

-continued

```
            225                 230                 235                 240
Arg Ser Ala Asp Gly Lys Gly Met Leu Leu Ala Asn Pro His Phe Pro
                245                 250                 255
Trp Asn Gly Ala Met Arg Phe Tyr Gln Met His Leu Thr Ile Pro Gly
                260                 265                 270
Arg Leu Asp Val Met Gly Ala Ser Leu Pro Gly Leu Pro Val Val Asn
                275                 280                 285
Ile Gly Phe Ser Arg His Leu Ala Trp Thr His Thr Val Asp Thr Ser
                290                 295                 300
Ser His Phe Thr Leu Tyr Arg Leu Ala Leu Asp Pro Lys Asp Pro Arg
305                 310                 315                 320
Arg Tyr Leu Val Asp Gly Arg Ser Leu Pro Leu Glu Lys Ser Val
                325                 330                 335
Ala Ile Glu Val Arg Gly Ala Asp Gly Lys Leu Ser Arg Val Glu His
                340                 345                 350
Lys Val Tyr Gln Ser Ile Tyr Gly Pro Leu Val Val Trp Pro Gly Lys
                355                 360                 365
Leu Asp Trp Asn Arg Ser Glu Ala Tyr Ala Leu Arg Asp Ala Asn Leu
                370                 375                 380
Glu Asn Thr Arg Val Leu Gln Gln Trp Tyr Ser Ile Asn Gln Ala Ser
385                 390                 395                 400
Asp Val Ala Asp Leu Arg Arg Val Glu Ala Leu Gln Gly Ile Pro
                405                 410                 415
Trp Val Asn Thr Leu Ala Ala Asp Glu Gln Gly Asn Ala Leu Tyr Met
                420                 425                 430
Asn Gln Ser Val Val Pro Tyr Leu Lys Pro Glu Leu Ile Pro Ala Cys
                435                 440                 445
Ala Ile Pro Gln Leu Val Ala Glu Gly Leu Pro Ala Leu Gln Gly Gln
                450                 455                 460
Asp Ser Arg Cys Ala Trp Ser Arg Asp Pro Ala Ala Gln Ala Gly
465                 470                 475                 480
Ile Thr Pro Ala Ala Gln Leu Pro Val Leu Leu Arg Arg Asp Phe Val
                485                 490                 495
Gln Asn Ser Asn Asp Ser Ala Trp Leu Thr Asn Pro Ala Ser Pro Leu
                500                 505                 510
Gln Gly Phe Ser Pro Leu Val Ser Gln Glu Lys Pro Ile Gly Pro Arg
                515                 520                 525
Ala Arg Tyr Ala Leu Ser Arg Leu Gln Gly Lys Gln Pro Leu Glu Ala
                530                 535                 540
Lys Thr Leu Glu Glu Met Val Thr Ala Asn His Val Phe Ser Ala Asp
545                 550                 555                 560
Gln Val Leu Pro Asp Leu Leu Arg Leu Cys Arg Asp Asn Gln Gly Glu
                565                 570                 575
Lys Ser Leu Ala Arg Ala Cys Ala Ala Leu Ala Gln Trp Asp Arg Gly
                580                 585                 590
Ala Asn Leu Asp Ser Gly Ser Gly Phe Val Tyr Phe Gln Arg Phe Met
                595                 600                 605
Gln Arg Phe Ala Glu Leu Asp Gly Ala Trp Lys Glu Pro Phe Asp Ala
                610                 615                 620
Gln Arg Pro Leu Asp Thr Pro Gln Gly Ile Ala Leu Asp Arg Pro Gln
625                 630                 635                 640
Val Ala Thr Gln Val Arg Gln Ala Leu Ala Asp Ala Ala Glu Val
                645                 650                 655
```

```
Glu Lys Ser Gly Ile Pro Asp Gly Ala Arg Trp Gly Asp Leu Gln Val
            660                 665                 670

Ser Thr Arg Gly Gln Glu Arg Ile Ala Ile Pro Gly Gly Asp Gly His
        675                 680                 685

Phe Gly Val Tyr Asn Ala Ile Gln Ser Val Arg Lys Gly Asp His Leu
        690                 695                 700

Glu Val Val Gly Gly Thr Ser Tyr Ile Gln Leu Val Thr Phe Pro Glu
705                 710                 715                 720

Glu Gly Pro Lys Ala Arg Gly Leu Leu Ala Phe Ser Gln Ser Ser Asp
                725                 730                 735

Pro Arg Ser Pro His Tyr Arg Asp Gln Thr Glu Leu Phe Ser Arg Gln
                740                 745                 750

Gln Trp Gln Thr Leu Pro Phe Ser Asp Arg Gln Ile Asp Ala Asp Pro
        755                 760                 765

Gln Leu Gln Arg Leu Ser Ile Arg Glu
        770                 775

<210> SEQ ID NO 6
<211> LENGTH: 33
<212> TYPE: DNA
<213> ORGANISM: Artificial Sequence
<220> FEATURE:
<223> OTHER INFORMATION: Forward Primer for the QsbA gene

<400> SEQUENCE: 6
cgtggatcca tgatgcagga ttcgccgctg cgc                                33

<210> SEQ ID NO 7
<211> LENGTH: 32
<212> TYPE: DNA
<213> ORGANISM: Artificial Sequence
<220> FEATURE:
<223> OTHER INFORMATION: Reverse Primer for the QsbA gene

<400> SEQUENCE: 7
cgcgaattca ccggcagccc tcatgcgaca ac                                 32
```

RALSTONIA AHL-ACYLASE GENE

BACKGROUND OF THE INVENTION

1. Field of the Invention

This invention pertains to the field of molecular biology. In particular, the invention relates to an N-acyl homoserine lactone acylase gene from *Ralstonia* sp. XJ12B.

2. Description of the Background Art

N-acyl homoserine lactones (AHLs), also known as auto-inducers, are widely used quorum sensing signal molecules in many Gram-negative bacteria. These compounds regulate certain classes of target genes in bacteria, such as virulence genes or biofilm differentiation genes. Generally, quorum sensing molecules are highly conserved and share an identical homoserine lactone moiety. The length and structure of their acyl side chains are different, however. Although the target genes regulated by AHLs in different bacteria species are varied, basic mechanisms of AHL biosynthesis and gene regulation are conserved among different bacterial species.

The general feature of AHL-mediated gene regulation is that it is cell population dependent (quorum sensing). Bacteria secrete AHLs into the environment; extracellular concentration of AHLs increases as bacterial cell populations grow. When AHL accumulates to a threshold extracellular concentration, the expression of certain sets of target genes are triggered in the bacteria.

Bacteria using these signals release, detect and respond to the accumulation of AHL signal molecules for synchronizing expression of a particular sets of genes and coordinating cellular activities within the bacterial cell population. AHLs are involved in regulation of a range of biological functions, including bioluminescence in *Vibrio* species (13, 4), Ti plasmid conjugal transfer in *Agrobacterium tumefaciens* (31), induction of virulence genes in *Burkhholderia cepacia, Erwinia carotovora, Erw. chrysanthemi, Erw. stewartii, Pseudomonas aeruginosa,* and *Xenorhabdus nematophilus* (3, 6, 12, 17, 19, 22, 23, 24, 26), regulation of antibiotic production in *P. aureofaciens* and *Erw. carotovora* (6, 26), swarming motility in *Serratia liquifaciens* (14) and biofilm formation in *P. fluorescens* and *P. aeruginosa* (1, 8). In many other bacterial species the relevant biological functions controlled by AHLs remain to be investigated (2, 5, 11).

A number of plant, animal and human bacterial pathogens use AHL quorum-sensing signals to regulate expression of pathogenic genes and aid in the formation of biofilms. Therefore, AHL quorum-sensing signal molecules are group of molecular targets for genetic and chemical manipulations since disruption of these signaling mechanisms can prevent or reduce the ability of these bacteria to infect plant and animal tissues or to form biofilms.)

The gene encoding an AHL-inactivation enzyme (AiiA) from a Gram-positive bacterium (*Bacillus* strain 240B1) has been cloned (9). AiiA (also known as AHL-lactonase) inactivates AHL activity by hydrolyzing the lactone bond of AHLs (10). Expression of aiiA in transformed *Erw. carotovora* (a pathogenic strain which causes soft rot disease in many plants) significantly reduces the release of AHL, decreases extracellular pectrolytic enzyme activities, and attenuates pathogenicity on potato, eggplant, Chinese-cabbage, carrot, celery, cauliflower, and tobacco (9). Transgenic plants expressing AHL-lactonase showed a significantly enhanced resistance to *Erw. carotovora* infection and delayed development of soft rot symptoms (10). AHL-inactivation mechanisms appear to be widely distributed. For example, a bacterial isolate of *Variovorax paradoxus* was reported to use AHL molecules as its energy and nitrogen sources, indicating the possible presence of AHL-degrading enzymes (18).

Further methods to counteract AHL-mediated plant, animal and human disease and plant pathogen virulence by interfering with bacterial intercellular communication would be highly desirable.

SUMMARY OF THE INVENTION

Accordingly, in this study, the cloning and characterization of a gene encoding an AHL-acylase from a bacterial isolate *Ralstonia* sp. JX12B is reported.

In one embodiment, the invention provides a composition of matter which comprises a nucleic acid according to SEQ ID NO: 1. In another embodiment, the invention provides a composition of matter which comprises a nucleic acid selected from the group consisting of nucleotides 1234–3618 of SEQ ID NO: 1, a fragment thereof and a substantially homologous variant thereof.

In yet a further embodiment, the invention provides a nucleic acid according to claim 2 which comprises nucleotides 1234–3618 of SEQ ID NO: 1.

In yet a further embodiment, the invention provides a composition of matter which comprises a peptidic sequence selected from the group consisting of a peptidic sequence according to SEQ ID NO: 2, a fragment thereof and a substantially homologous variant thereof.

In yet a further embodiment, the invention provides a composition of matter which comprises a peptidic sequence encoded by a nucleic acid selected from the group consisting of nucleotides 1234–3618 of SEQ ID NO: 1, a fragment thereof and a substantially homologous variant thereof.

In yet a further embodiment, the invention provides a composition of matter which comprises a peptidic sequence selected from the group consisting of SEQ ID NO: 2, a fragment thereof, a subunit thereof and a substantially homologous variant thereof, such as a peptidic sequence according to SEQ ID NO: 2, a peptidic sequence comprising amino acids 36–217 233–794[?] of SEQ ID NO: 2 or a peptidic sequence comprising amino acids 233–794 of SEQ ID NO: 2.

In yet a further embodiment, the invention provides a composition of matter as described above which inactivates AHL.

In yet a further embodiment, the invention provides a method of modulating AHL signaling activity which comprises contacting said AHL with a composition of matter as described above.

In yet a further embodiment, the invention provides a transgenic plant or non-human mammal harboring a nucleic acid as described above.

In yet a further embodiment, the invention provides a method of controlling a bacterial disease in a mammal which comprises administering to said mammal a composition of matter as described above, wherein the expression of pathogenic genes of said bacteria are regulated by AHL signals.

In yet a further embodiment, the invention provides a method of controlling a bacterial disease in a plant which comprises administering to said plant a composition of matter as described above, wherein the expression of pathogenic genes of said bacteria are regulated by AHL signals.

BRIEF DESCRIPTION OF THE DRAWINGS

FIG. 1 is a photograph showing AHL inactivation bioassay results for bacterial cultures and bacterial proteins from the indicated bacterial clones.

DETAILED DESCRIPTION OF THE PREFERRED EMBODIMENTS

Figure 1A:
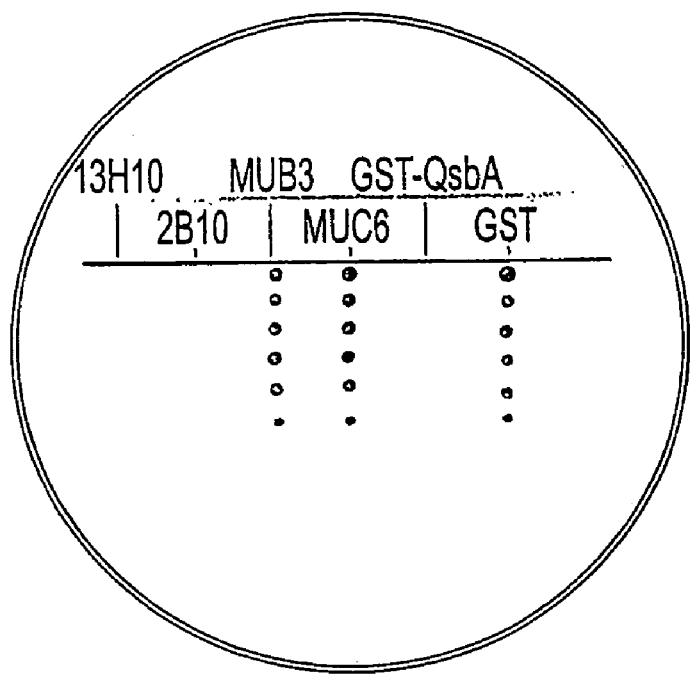
FIG. 1A shows the results of a bioassay with bacterial cultures of *E. coli* DH5α strains 13H10 (slice 1), 2B10 (slice 2), MUB3 (slice 3), MUC6 (slice 4), GST-QsbA (slice 5) and GST (slice 6), which contain plasmid clones or constructs p13H10, p2B10, pMUB3, pMUC6, pGST-QsbA, and pGST, respectively.

A bacterial isolate of *Ralstonia* sp. XJ12B from a biofilm sample in a water treatment system was found to enzymatically inactivate AHLs, bacterial quorum-sensing molecules, in a bioassay using *Agrobacterium tumefaciens* strain Nt1 (traR; tra:lacZ749) as an indicator for AHL activity. The gene encoding the protein exhibiting this enzyme activity for AHL inactivation (qsbA) was cloned from a bacterial strain isolated from the biofilm sample and found to encode a peptide of 794 amino acids.

Bacterial cultures and bacterial proteins were assayed for the ability to inactivate AHL using *Agrobacterium tumefaciens* indicator cells. A tumefaciens was cultured at 28° C. in MM medium as described in Zhang et al. (31). The bacteria or protein to be assayed is first mixed with an AHL substrate, for example N-β-oxooctanoyl-L-homoserine lactone (OOHL), and the reaction (inactivation of the AHL) is allowed to proceed. If AHL inactivation activity is present in the sample (i.e. the AHL has been cleaved and inactivated), then the inactivated AHL products fail to trigger the expression of lacZ reporter gene which is under the control of a TraR-dependent promoter. The strain *A. Tumefaciens* NT1 hosting the lacZ reporter system therefore does not turn blue in the presence of substrate 5-bromo-4-chloro-3-indolyl β-D-galactopyranoside (X-gal). See Example 2 for details of the bioassay. Any AHL may be used in the assay, as desired. Of course, any suitable assay for cleavage of AHL, including traditional in vitro enzyme assays may be used to detect the AHL inactivation activity. Those of skill in the art are able to modify or devise assays to detect and/or quantitate AHL inactivation.

*Escherichia coli* strain DH5a was used as a host for DNA manipulation. Both *Ralstonia* sp. and *E. coli* were cultured in LB medium (tryptone, 10 g/L, yeast extract, 5 g/L, and NaCl, 10 g/L, pH 7.0) at 37° C. Appropriate antibiotics were added when necessary at the following concentrations: ampicillin, 100 µg/ml; tetracycline, 10 µg/ml; and kanamycin, 20 µg/ml.

The gene encoding the protein responsible-for the detected AHL inactivation was isolated using a cosmid library of 1600 clones with the genomic DNA of *Ralstonia* sp. strain XJ12B, constructed in *E. coli*. *E. coli* transfectants were screened for the ability to inactivate AHL. One clone, p13H10, was found to inactivate AHL. Cosmid DNA from p13H10 was digested, fused into a cloning vector, ligated and transformed into *E. coli*. The *E. coli* clones again were assayed for AHL inactivating activity. One clone, containing a 4 kb insert, had AHL inactivation activity.

Plasmids were subsequently purified for sequencing. The 4 kb fragment from clone p2B10 was completely sequenced according to known methods using ABI Prism dRhodamine Terminator Cycle Sequencing Ready Reaction Kit (Perkin-Elmer Applied Biosystems). See Table I, below. The sequence contained an open reading frame of 2385 nucleotides which was the AHL inactivation gene, qsbA, encoding a predicted polypeptide of 794 amino acids (85,373 Daltons).

TABLE I

| QsbA Gene (*Ralstonia* sp.) Nucleotide Sequence (SEQ ID NO: 1). | |
|---|---|
| gtttgggaaagtgggnagcgcgctgtgcag cgccccgcccctcagccgcgcagctcggcg cgcaccgaatgcgcgcgccggtgggcgccc | 90 |
| ggcggctggccggtgtggcgccggatcagg cgccggaaggcggacatgtcgtgataaccg cactgttcggcgattgccgtcaggctcagc | 180 |
| gtgctgacttccagcaggtggcaggcgcgc tccacgcgcagccggtgcagcaattgcagc ggcgaggtgcccagggtcttggtgaaatgc | 270 |
| cgcagcagcgtgcgctcgctggtcgaggcg gcggcggccagcttggccaggtcgaacggc tcgtgcaggtgctgctgcaggtagcgccgc | 360 |
| gcccgcagtaccacgctggtgcggatggcg ggcttgctgcgcagccagatggcggtggac tcaccgcgcgacgggtggtcgagcacggcc | 450 |
| tggccgagggtgcgtgccagccgggtgtcg gccaggcggccgaccaggcgctgcgtgagc gccacgccgtgctccatcgcgcgcgccgtc | 540 |
| agcacgttgccgctgctgacgatggcctgc tccgccaccaccttcagctgcgggtagttg ccgtgcagccagccggcgatcagccacgtc | 630 |
| accgtcaagcgccggccggcgggcagcgcg ccggccagcagcgccacgccggtgaaggac gaggccaccaagcctgccggcgtccaggta | 720 |
| gcgccggatggtggcgcgttcccactccag cagggccaggcgctgctccagcgtgctgat gtggtcgaaatgcaggggcgggacgaccag | 810 |
| cgcgtcgcccagcgcggcgtcgcccgccgg cagcggctggcagcggcaggccagggtctc ggcggcggcctgccagcgggccgggtcgcg | 900 |
| cgcgaccagccgccacccgaacaccgggct ggcggcatcggcacgcttgccggcatgcat ggaggcgagcgcattggccacgccgagggt | 990 |
| gtcggcgacggtcgccagcgtggagaggcc ggcgtcgggaaaggtcagcaggtcgatgtc ggcatccgcaaagtataggggaggcgggcg | 1080 |
| gaggcctcctgcgtggcgggattgacccca actctggcgggaatacctctttcctccggg cgggccccagtcgacgatacggcggtggct | 1170 |
| gcgcctgcgcgccgccgcaagactagagcg acacaagacaagaccgacaac<u>aggaga</u>caa cgcATGATGCAGGGATTCGCGCTGCGCGGC | 1260 |
| ACGCTCGCCATGGCCGCGCTCGCGGCGCTG GCCGGCTGCGCCAGTTCCACCGATGGCCGC TGGGGGTCGCTCAGCGACACCGGCCTGTCC | 1350 |
| GCCGAGATCCGCCGCACCGGCTTCGGCATT CCGCACATCCGCGCCAACGACTACGCCAGC CTCGGCTATGGCATGGCCTATGCCTACGCG | 1440 |
| CAGGACAACCTGTGCCTGCTGGCCGACCAG GTGGTCACCGTCAACGGCGAGCGCTCGAAG ACCTTCGGGCCCGAGGGCACCGTGACGGTC | 1530 |
| TCGTTCAAGCCGATCCCCAACCTGCAGTCG | 1620 |

TABLE I-continued

QsbA Gene (*Ralstonia* sp.) Nucleotide Sequence (SEQ ID NO: 1).

| Sequence | Position |
|---|---|
| GACGCCTTCTTCAAGGGCATCTTCGACGAG GACGGCCTGCGCGCCGGTTATGCGCAGATG | |
| TCGCCCGAGGCGCGCGAGCTGCTGCGCGGC TACATCGCCGGCTTCAACCGCTATCTCAAG GACACGCCGCCCGCCAACTTCCCGGCCGCC | 1710 |
| TGCCGCAATGCCGCCTGGGTGCGTCCGCTC ACGCTGGGCGACATGATGCGCATGGGCGAA GAGAAGGCGATCCAGGCCAGCGCCGGCGCC | 1800 |
| ATGCTGGCGGGCATCGTCGCCGCGCAGCCG CCGGGCCGCACGCCGGTGGCCGAGCGCGAG ATTCCGCCGCAGGCCGTCGACACCGTGGCG | 1890 |
| CTGGACCGCGAACTGCAGCTGCGCGACATG CCGATCGGCTCCAACGGCTGGGCCTTCGGC GCTGACGCCACCGCCAACCGGCGCGGCGTG | 1980 |
| CTGCTCGGCAATCCGCACTTCCCGTGGACG ACCACCAACCGCTTCTACCAGGTCCACCTG ACGGTGCCCGGCAAGCTCGACGTGATGGGC | 2070 |
| GCCTCGATCGCGGCCTTCCCGGTGGTGAGC ATCGGCTTCAACAAGGACGTGGCGTGGACG CACACCGTCTCCACCGGCCGCCGCTTCACC | 2160 |
| TTGTTCGAACTGAAGCTGGCCGAAGGCGAC CCGACCACCTACCTGGTCGACGGCACGCCG CACAAGATGACCACCCGCACGGTCGCCTTC | 2250 |
| GACGTGAAGCTGCCGGACGGCGCCTCGAG CGCCGCACGCACACCTTCTACGACACCATC TACGGCCCGGTGCTGTCGATGCCGAGCGGC | 2340 |
| GGCATGCCGTGGACCACGCAGAAGGCCTAC GCCCTGCGCGACGCCAACCGCAACAACACG CGCTCGGTCGACAGCTGGCTGCATATCGGG | 2430 |
| CAGGCCCGGGACGTGGCCGGCATCCGCCAG GCCATCGGCAACCTGGGCATTCCCTGGGTC AACACCATCGCCACCGACCGCAACGGCCGC | 2520 |
| GCGCTGTTCGCCGACGTGTCGACCACGCCG GACGTGCCGGCCGCGGAGCTCCAGCGCTGT GCCCCGTCGCCGCTGGCCGGCAAACTCTTC | 2610 |
| AAGGACGCGGGCCTGGTGCTGCTCGACGGC TCGCGCGGCACCTGCAACTGGCAGGTCGAT CCGGCTTCGCCGGTACCCGGGCTGGTGGCG | 2700 |
| CCCGCGCGCATGCCGGTGCTCGAGCGCGAC GACTACGTCGCCAACAGCAATGACAGCTCC TGGCTGACCAACCCCGCGCAAAAGCTGACC | 2790 |
| GGCTTCTCGCCGGTGATGGGCTCGGTCGAC GTACCGCAGCGGCTGCGCACGCGCATCGGC CTGATCGAGATCGGCCGCCGCCTGGCCGGC | 2880 |
| ACCGACGGACTGCCCGGCAACCGCATCGAT CTGCCGAACCTGCAGGCGATGATCTTCAGC AATGCCAACCTGGCGGGACAACTGGTGCTG | 2970 |
| GGCGACCTGCTCGCGGCATGCAAGGCCACG CCGGCCCCGGATGCCGACGTGCGCGACGGC TGCGCCGCCCTCGGCCAGTGGAACCGCACC | 3060 |
| AGCAACGCCGACGCCCGCGCCGCGCACCTG TTCCGCGAGTTCTGGATGCGCGCCAAGGAC ATCGCGCAGGTGCACGCCGTCGAGTTCGAC | 3150 |
| CCGGCCGACCCGGTCCACACGCCGCGCGGC CTGCGCATGAACGACGCGACGGTACGCACG GCGGTGTTCAAGGCGCTGAAGGAAGCCGTG | 3240 |
| GGCGCGGTGCGCAAGGCGGGCTTCGCGCTG | 3330 |
| GATGCGCCGCTGGGCACGGTACAGGCCGCG CACGCACCGGACGGCTCCATCGCCCTGCAC | |
| GGCGGCGAGGAATACGAAGGCGTGCTCAAC AAGCTGCAAACCCTGCCGATCGGGCCGAAG GGGCTGCCGGTGTATTTCGGCACCAGCTAC | 3420 |
| ATCCAGACCGTGACCTTCGACGACCAGGGC CCGGTCGCCGACGCCATCCTCACCTACGGC GAATCGACCGACCACGCCTCGCCGCACGCG | 3510 |
| TTCGACCAGATGCGTGCGTACTCGGGCAAG CACTGGAACCGGCTGCCGTTCTCCGAAGCG GCCATCGCGGCCGATCCGGCGCTGAAGGTG | 3600 |
| ATGCGGTTGTCGCAGTGAgggctgccggtg cctggaaaaacgccccgcttgtgcgggcg ttttttgccagtgtgaatggctcaatcgt | 3690 |
| gttggaaaccgcatccggacatgactgtat tgtgactctgcctgtgtccgtgt | 3743 |

The predicted open reading frame of the qsbA gene is shown in upper case letters with the start codon and stop codon in bold. A putative ribosome binding site (AGGAGA) is underlined.

Sequence analysis of this peptide indicated that QsbA did not have any significant homology with the known AHL-lactonase quorum-sensing molecule inactivator encoded by the aiiA gene from *Bacillus* sp. 240B1, however the deduced peptide sequence was typical of the primary structure of aculeacin A acylases (AACs) and penicillin G acylases, with signal peptide-α subunit-spacer-β subunit organization (16, 30). The Ralstonia sequence shares substantial identity with AACs from *Deinococcus radiodurans* strain R1, *Actinoplanes utahensis* and a putative acylase from *Pseudomonas aeruginosa*, all of which catalyze deacylation of their substrates. These AAC genes are translated as single precursor polypeptide and then processed to the active form, which has two subunits. Aculeacin A is an echinocandin-type antifungal antibiotic with a long fatty side chain. Aculeacin A acylases purified from *A. utahensis* catalyze the hydrolysis of the amide bond on the palmitoyl side chain of aculeacin A (29). The primary structure of the protein, as well as enzyme activity analysis with different substrates, discussed below, therefore indicates that qsbA encodes an AHL-acylase which cleaves the amide linkage between the acyl side chain and the homoserine lactone moiety of AHLs.

The presumed α and β subunits of QsbA are located at amino acid positions 36–217 and 233–794, respectively, of SEQ ID NO: 2, with a 15 amino acid spacer between them, as determined by alignment with the peptide sequences from *D. radiodurans* strain R1, *A. utahensis* and *P. Aeruginosa*. See Table II.

TABLE II

Aligned Amino Acid Sequences of QsbA from *Ralstonia* sp. XJ12B (SEQ ID NO: 2), *D. radiodurans* strain R1 acylase (SEQ ID NO: 3), *A. utahensis* acylase (SEQ ID NO: 4) and *P. aeruginosa* acylase (SEQ ID NO: 5).

```
R. sp   MMQGF---ALRGTLAMAALAALAGCA-----SSTDGRWGSLSDTGLSAEIRRTGFGIPHIRANDYASLGYGMAYAYAQDN   72
D. rad  MSR-----SPFSSVSLPARLLLGSLL-----LGPLMLGGAASAQTYQVQIQRTAHGIPHIQASDLGGIGYGVGYSYAQDN   70
A. uta  MTSSY---MRLKAAAIAFGVIVATAA-----VPSPAS-GREHDGGYAALIRRASYGVPHITADDFGSLGFGVGYVQAEDN   71
P. aer  MSRPFRPPLCRETTSMGMRTVLTGLAGMLLGSMMPVQADMPRPTGLAADIRWTAYGVPHIRAKDERGLGYGIGYAYARDN   80
         *       : ::      :            .     . *: ...*:*** *.*  .:*:*::.*  *.**

R. sp   LCLLADQVVTVNGERSKTFGPEGTVTVSFKPIPNLQSDAFFKGIFDEDGLRAGYAQMSPEARELLRGYIAGFNRYLKDTP   152
D. rad  LCLLADQVMTVRGERSKFLGAEGKTVVGFQPVNNLDSDVFFKTVIEPGRLQAGYRDQ-PQILALMRGYVAGVNRYLRDTP   149
A. uta  ICVIAESVVTANGERSRWFGATGPDDADVRTTSSTQAIDDRVAERLLEGPRDGVRAPCDDVRDQMRGFVAGYNHFLRRTG   151
P. aer  ACLLAEEIVTARGERARYFGSEGKSSAELD---NLPSDIFYAWLNQPEALQAFWQAQTPAVRQLLEGYAAGFNRFLREAD   157
         *::*:.::*..***.:: :*. *   ..   .  :

R. sp   PANFP-AACRNAAWVRPLTLGDMMRMGEEKAIQASAGAMLAGIVAAQPPGRTPVAEREIPPQAVDTVALDRELQLRDMPI   231
D. rad  PEQWP-SACRNADWVRPLTELDVMRLGEEKAIQASAGAMVSAITSARPPQ----AGASTAAPRPDLAAFNRQYRFNDLPI   224
A. uta  VHRLTDPACRGKAWVRPLSEIDLWRTSWDSMVRAGSGALLDGIVAATPPT---AAGPASAPEAPDAAAIAAALDGTSAGI   228
P. aer  GKTTS---CLGQPWLRAIATDDLLRLTRRLLVEGGVGQFADALVAAAPPG----AEKVALSGEQAFQVAEQRRQRFRLER   230
         . *  . *:*.:: *: *     :... * :  ..:..:* **      *    .       .
                                                         ↑--------

R. sp   GSNGWAFGADATANRRGVLLGNPHFPWTTTNRFYQVHLTVPGKLDVMGASIAAFPVVSIGFNKDVAWTHTVSTGRRFTLF   311
D. rad  GSNGWAFGSEATTNGRGLLLGNPHFPWETSNRFYQLHLTLPGQFDVMGASLGGMPVVNIGFNQDVAWTHTVSTDKRFTLA   284
A. uta  GSNAYGLGAQATVNGSGMVLANPHFPWQGAERFYRMHLKVPGRYDVEGAALIGDPIIEIGHNRTVAWSHTVSTARRFVWH   288
P. aer  GSNAIAVGSERSADGKGMLLANPHFPWNGAMRFYQMHLTIPGRLDVMGASLPGLPVVNIGFSRHLAWTHTVDTSSHFTLY   290
         ***. ..*:: :.:  *::*.*****  : ***::**.:**: ** **::  . *:..**..: :**:***.*   :*.

R. sp   ELKLAEGDPTTYLVDGTPHKMTTRTVAFDVKLPDGRLERRTHTFYDTIYGPVLSMPSGGMPWTTQKAYALRDANRNNTRS   391
D. rad  ALTLVPGDPLSYVKDGQQRRLQRRTAVIEVKTANG-PRLHTRTVYFTPEGPLVNLPAAGLTWTPQYAFALRDANRNNTRM   383
A. uta  RLSLVPGDPTSYYVDGRPERMRARTVTVQTGSG-----PVSRTFHDTRYGPVAVVP-GTFDWTPATAYAITDVNAGNNRA   383
P. aer  RLALDPKDPRRYLVDGRSLPLEEKSVAIEVRGADGKLSRVEHKVYQSIYGPLVVWP-GKLDWNRSEAYALRDANLENTRV   390
         * *   ** *  * **       : ::...:.           :...: :   **:    *  . :  *. *:* *.* *.*

R. sp   VDSWLHIGQARDVAGIRQAIG-NLGIPWVNTIATDRNGRALFADVSTTPDVPAAELQRCAPSPLAGKLFKDAGLVLLDGS   470
D. rad  LATWLGFAGAKSVRDIRASLN-VQGIPWVNTIAADRAGSALYADISSSPNVSAAQQQACTPPPLA-PLFPAAGLAVLDGS   461
A. uta  FDGWLRMGQAKDVRALKAVLDRHQFLPWVNVIAADARGEALYGDHSVVPRVTGALAAACIPAPFQ-PLYASSGQAVLDGS   461
P. aer  LQQWYSINQASDVADLRRRVEALQGIPWVNTLAADEQGNALYMNQSVVPYLKPELIPACAIPQLV-----AEGLPALQGQ   464
         . *  : * .*  :: :    :****.:*:*   * **: *   * :         * .:          *  *:*.

R. sp   RGTCNWQVDPASPVPGLVAPARMPVLERDDYVANSNDSSWLTNPAQKLTGFSPVMGSVDVPQRLRTRIGLIEIGRRLAGT   550
D. rad  HSACDWKTDPASRVPGLRAPDKMPVLIRQDFVANSNNSAWLANPAAPQTGLDPLVGEVNAPQSPRTRMGLLEIGRRLSGT   541
A. uta  RSDCALGADPDAAVPGILGPASLPVRFRDDYVTNSNDSHWLASPAAPLEGFPRILGNERTPRSLRTRLGLDQIQQRLAGT   541
P. aer  DSRCAWSRDPAAAQAGITPAAQLPVLLRRDFVQNSNDSAWLTNPASPLQGFSPLVSQE-KPIGPRARYALSRLQGKQP--   543
         .  *    **   .:  . :** * *:* ***:* **:.**      *: ::..

R. sp   DGLPGNRIDLPNLQAMIFSNANLAGQLVLGDLLAACKATPAPDAD------VRDGCAALGQWNRTSNADA-RAAHLFREF   630
D. rad  DGLPGRTFDIPTLQATLLRESNLTGEMYAADAAKLCQS--AGGAE------LQPACNALAAWDRRSSQES-RGAALWREF   619
A. uta  DGLPGKGFTTARLWQVMFGNRMHGAELVRDDLVALCRRQPTATASNGAIVDLTAACTALSRFDERADLDS-RGAHLFTEF   621
P. aer  -------LEAKTLEEMVTANHVFSADQVLPDLLRLCRDN-QGEKS------LARACAALAQWDRGANLDSGSGFVYFQRF   613
                :   *   *   :    .:  *  *:    .         :  .*  **. ::. :.  ::  .   :   .*

R. sp   WMRAKDIAQVHAVEFDPADPVHTPRGLR-MNDATVRTAVFKALKEAVGAVRKAGFALDAPLGTVQAAHAPDGSIALHGGE   702
```

TABLE II-continued

Aligned Amino Acid Sequences of QsbA from *Ralstonia* sp. XJ12B (SEQ ID NO: 2), *D. radiodurans* strain R1 acylase (SEQ ID NO: 3), *A. utahensis* acylase (SEQ ID NO: 4) and *P. aeruginosa* acylase (SEQ ID NO: 5).

```
D. rad   WRRARAIPNVYAVPFDPADPVNTPRGLN-TADPAAQTALLGALREAAAALTAAGIPFDAPLGEVQGVVRGGDFISLPGGA    691

A. uta   LAGG----IRFADTFEVTDPVRTPAPFWNTTDPRVRTALADACNGSPASPSTR------SVGDIHTDSRGERRIPIHGGR    690

P. aer   MQRFAELDGAWKEPFDAQRPLDTPQGIA-LDRPQVATQVRQALADAAAEVEKSGIPDGARWGDLQVSTRGQERIAIPGGD    686
              *:    *:  **    :       . . *  :  *     :  .             *  ::          *  . :  **

R. sp    EYEGVLNKLQTLPIGPKGLPVYFG--TSYIQTVTFDDQGPVADAILTYGESTDHASPHAFDQMRAYSGKHWNRLPFSEAA    780

D. rad   EFEGVLDKIDFNPLAPGGYRGVVGNASSYIQTVGFTDSGVQAEAVLTYSQSSNPESPYFSDQTRLFSRSEWVKLPFTQPE    771

A. uta   GEAGTFNVITNPLVPGVGYPQVVHG-TSFVMAVELGPHGPSGRQILTYAQSTNPNSPWYADQTVLYSRKGWDTIKYTEAQ    769

P. aer   GHFGVYNAIQS--VRKGDHLEVVGG-TSYIQLVTFPEEGPKARGLLAFSQSSDPRSPHYRDQTELFSRQQWQTLPFSDRQ    763
           *.  : :       :     .     . :*::  *  :   *   . :*::..:*::  **   **    :*  .  *    : :::

R. sp    IAADPALKVMRLSQ---                                                                 794

D. rad   IEADPTRTVVQLSE---                                                                 785

A. uta   IAADPNLRVYRVAQRGR                                                                 786

P. aer   IDADPQLQRLSIRE---                                                                 777
           * ***                :   :
```

* = identical residues, : = conserved substitutions; . = semi-conserved substitutions; ↑ = post-translational processing sites for signal peptide and subunits; - = spacers.

Figure 1B:
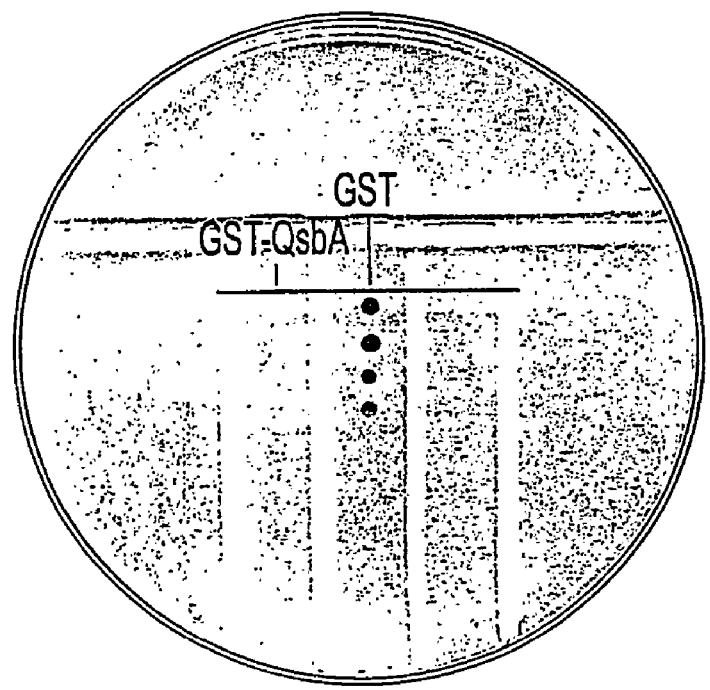
FIG. 1B shows results for bioassay of the indicated bacterial proteins GST-QsbA and GST.

The coding region of the qsbA gene was amplified by PCR. The amplified PCR products were digested, fused in-frame to the coding sequence of the glutathione S-transferase (GST) gene and expressed in *E. coli*. Protein extracts from the recombinant *E. coli* cells were assayed for the ability to inactivate AHL. Protein from *E. coli* expressing GST alone served as a control. The results demonstrated that GST-QsbA fusion protein effectively eliminated AHL activity. See FIG. 1B.

The substrate specificity of QsbA was determined by assaying total soluble protein extracted from the recombinant *E. coli* (pGST-QsbA) for inactivation of AHLs using substrates with acyl chains of differing lengths. QsbA was able to completely inactivate 3-oxo group acyl-HSLs having acyl chains of 8, 10 and 12 carbons. QsbA also strongly inactivated methylene group acyl-HSLs having acyl chains of 8 and 10 carbons. QsbA also inactivated the butyl and hexyl esters of N-β-octanoyl-L-homoserine, whereas the AHL-lactonase encoded by aiiA was unable to inactivate them. The substrate specificity data indicate that QsbA is an AHL-acylase.

QsbA and qsbA provide new tools for down regulation of AHL-mediated biological activities, such as the expression of virulence genes and biofilm differentiation in pathogenic bacteria, both in vitro and in vivo. The qsbA gene, which encodes the AHL inactivation enzyme (QsbA), or a functional fragment, subunit or substantially homologous variant thereof, may be introduced into a plant genome to produce a genetically modified plant with the ability to quench pathogen quorum-sensing signaling. Transgenic plants expressing an enzyme that inactivates AHLs can exhibit a significantly enhanced resistance to infection by bacterial pathogens, even when bacteria are present in high concentrations.

Methods of genetic manipulation and transformation of plant cells are well known in the art, as are methods of regenerating fertile, viable transformed plants. In general, any method of cloning the coding region of qsbA or a functional fragment or substantially homologous variant thereof into a suitable expression vector may be used. It is convenient to ligate the qsbA coding region into a vector, followed by ligation into a plant transformation vector, however those of skill are well aware of alternative methods to achieve the same results. Any suitable plant transformation vector may be used. The vector contains the qsbA gene, or a functional fragment, subunit or substantially homologous variant thereof, so long as expression of the gene results in a QsbA protein or functional fragment, subunit or variant thereof which inactivates AHL.

A functional promoter preferably controls expression. Many suitable promoters are known in the art, such that a convenient promoter may easily be selected by a skilled artisan depending on the expression system being used. Such selection of a suitable promoter to achieve the desired level of translational expression is considered routine in the art. For example, it is advantageous to optimize qsbA expression by modification of codon usage and coupling to a strong promoter such as the double 35S promoter.

A suitable marker gene, such as kanamycin resistance, green fluorescent protein or any other convenient marker is advantageously used. Variations of the commonly used and well known methods for transforming plants with a gene, are well within the skill of the ordinary artisan in genetic manipulation of plants. Expression constructs may contain a signal sequence to direct secretion of the expressed QsbA protein, or may lack such a sequence, as desired. The plant transformation vectors containing the qsbA gene and a marker gene may be used to transform plant cells using *Agrobacterium*-mediated transformation. *Agrobacterium*-mediated transformation is conveniently used to transform plants with the qsbA gene, however any suitable method known in the art may be used, depending on the plant being transformed. For example, certain monocotyledonous plants are more efficiently transformed using other methods such as microprojectile bombardment, vacuum filtration or any other method known in the art to introduce and integrate DNA plasmids or fragments into the plant genome. Those of skill in the art are familiar with means to transform gymnosperms, monocots and dicots. All of these methods known in the art are contemplated for use with this invention.

After selection for transformants carrying the qsbA gene, transgenic plants may be regenerated according to known methods in the art. Plants selected for a marker gene, for example kanamycin resistance, may be assayed, for example by PCR and DNA gel blot to determine how many copies of the qsbA gene are present in the plant tissue. Any suitable method known in the art is contemplated for use with the gene of this invention. QsbA enzyme activity may be detected in transgenic plants transformed with the qsbA gene by the bioassay method described in Example 2 or by any convenient method.

By "functional fragment, subunit or substantially homologous variant thereof," when referring to a qsbA nucleotide sequence, it is meant any fragment, subunit, variant or homologous sequence of qsbA (nucleotides 1234–3618 of SEQ ID NO: 1) which encodes a protein or peptide sequence capable of inactivating N-acyl homoserine lactones. "Substantially homologous variants" of a nucleotide sequence generally are those the complement of which hybridizes with qsbA under stringent or highly stringent conditions, for example temperatures of about 30° C. to about 50° C., for example 30° C., 35° C., 37° C., 40° C., 45° C. or 50° C., and/or salt concentrations of about 200 mM to about 1000 mM NaCl or the equivalent ionic strength, for example 200 mM, 250 mM, 300 mM, 400 mM, 500 mM, 750 mM or 1000 mM. The stringency conditions are dependent on the length of the nucleic acid and the base composition of the nucleic acid and can be determined by techniques well known in the art. Those of skill in the art are familiar with these conditions and ranges which are useful. Generally, a substantially homologous nucleotide sequence is at least about 75% homologous to SEQ ID NO: 1 or a fragment or subunit thereof, preferably at least about 85% homologous, and most preferably 90%, 95% or 99% homologous or more.

Those of skill in the art are familiar with the degeneracy of the genetic code, and thus are aware that nucleic acid sequences may be less than 100% homologous and yet encode the same protein or peptide sequence. Such variation in any of the sequences, fragments, subunits or substantially homologous variants also are contemplated as part of this invention.

Peptide and protein sequences which are encompassed by this invention include any sequences encoded by the qsbA gene, or any fragment, subunit or substantially homologous variant thereof. Such sequences therefore include any functional protein or peptide which retains the ability to inactivate AHL, including protein and peptide fragments of the complete QsbA protein, such as, for example, the sequences of amino acids 36–217 and 233–794 encoding by SEQ ID NO: 1 and substantially homologous variants thereof. A substantially homologous variant of the QsbA protein includes sequences which are at least about 50% homologous, preferably at least about 60% homologous, and most preferably 70%, 80% or 90% homologous or more. Therefore, a protein which is a substantially homologous varient of QsbA is about 50% to about 99.9% homologous with QsbA. Both conservative and non-conservative amino acid substitutions are contemplated, as well as sequences containing non-traditional or modified amino acids such as those known in the art.

The term "fragment" is intended to indicate any portion of the nucleotide of SEQ ID NO: 1 or protein/peptide sequence of SEQ ID NO: 2 which is greater than about 300 nucleotide bases or about 100 amino acids, up to one nucleotide or amino acid less than the entire sequence. The term "subunit" is intended to encompass any functional unit of the QbsA protein, such as, for example, amino acids 36–217 or 233–794 of SEQ ID NO: 2.

A protein or peptide sequence which is considered to inactivate N-acyl homoserine lactones is one which is capable of inactivating at least 55 pmoles N-acyl homoserine lactone (OOHL) per µg protein per minute at 30° C.

It has been previously demonstrated that quenching bacterial quorum sensing by inactivation of N-acyl homoserine lactone with AHL-lactonase stops bacterial infection (9, 10). The gene and protein described here, which is likely an AHL-acylase, represent a new and effective tool for inactivation of AHL signals and thus control bacterial infection. Similarly, the gene and protein described here targets AHL quorum-sensing signals that regulate expression of pathogenic genes of many bacterial pathogens at a threshold concentration. This tool is applicable to all plant, animal or human diseases where the expression of pathogenic genes of bacterial pathogens is activated by AHL signals, such as, for example, plant pathogens *Erw. carotovora*, *Erw. Chrysanthemi*, *Erw. Stewartii*; human pathogens *P. aeruginosa*, *B. cepacia*; and animal pathogens *X. nematophilus*, *P. fluorescens* (1, 3, 6, 12, 17, 19, 22, 23, 24, 26).

REFERENCES

1. Allison, et al., "Extracellular products as mediators of the formation and detachment of *Pseudomonas fluorescens* biofilms," *FEMS Microbiol. Lett.* 167: 179–184, 1998.
2. Bassler, et al., "Cross-species induction of luminescence in the quorum-sensing bacterium *Vibrio harveyi*," *J. Bacteriol.* 179: 4043–4045, 1997.
3. Beck von Badman, and Ferrand, "Capsular polysaccharide biosynthesis and pathogenicity in *Erwinia stewartii* require induction by an N-acyl homoserine lactone autoinducer," *J. Bacteriol.* 177: 5000–5008, 1995.
4. Cao and Meighen, "Purification and structural identification of an autoinducer for the luminescence system of *Vibrio harveyi*," *J. Biol. Chem.* 264: 21670–21676, 1989.
5. Cha et al., "Production of acyl-homoserine lactone quorum-sensing signals by gram-negative plant associated bacteria," *Mol. Plant Microbe Interact.* 11: 1119–1129, 1998.
6. Costa and Loper, "EcbI and EcbR: homologs of LuxI and LuxR affecting antibiotic and exoenzyme production by *Erwinia carotovora* subsp. *betavasculorum*," *Can. J. Microbiol.* 43: 1164–1171, 1997.
7. Daumy et al., "Role of protein subunits in *Proteus retigeri* penicillin G acylase," *J. Bacteriol.* 163: 1279–1281, 1985.
8. Davies et al., "The involvement of cell-to-cell signals in the development of a bacterial biofilm," *Science* 280: 295–298, 1998.
9. Dong et al., "AiiA, an enzyme that inactivates the acyl homoserine lactone quorum-sening signal and attenuates the virulence of *Erwinia carotovora*," *Proc. Natl. Acad. Sci. USA* 97: 3526–3531, 2000.

10. Dong et al., "Quenching quorum sensing-dependent bacterial infection by an N-acyl homoserine lactonase," *Nature* 411: 813–817, 2001.

11. Dumenyo et al., "Genetic and physiological evidence for the production of N-acyl homoserine lactones by *Pseudomonas syringae* pv. *syringae* and other fluorescent plant pathogenic *Pseudomonas* species," *Eur. J. Plant Pathol.* 104: 569–582, 1998.

12. Dunphy et al., "A homoserine lactone autoinducer regulates virulence of an insect-pathogenic bacterium, *Xenorhabdus nematophilus* (Enterobacteriaceae)," *J. Bacteriol.* 179: 5288–5291, 1997.

13. Eberhard et al., Structural identification of autoinducer of *Photobacterium fischeri* luciferase," *Biochemistry* 20: 2444–2449, 1981.

14. Eberl et al., "Involvement of N-acyl-L-homoserine lactone autoinducers in controlling the multicellular behaviour of *Serratia liquefaciens*," *Mol. Microbiol.* 20: 127–136, 1996.

15. Fuqua and Winans, "Conserved cis-acting promoter elements are required for density-dependent transcription of *Agrobacterium tumefaciens* conjugal transfer genes," *J. Bacteriol.* 178: 435–440, 1996.

16. Inokoshi et al., "Cloning and sequencing of the aculeacin A acylase-encoding gene from *Actinoplanes utahensis* and expression in *Streptomyces lividans*," *Gene* 119: 29–35, 1992.

17. Jones et al., "The Lux autoinducer regulates the production of exoenzyme virulence determination in *Erwinia carotovora* and *Pseudomonas aeruginosa*," *EMBO J.* 12:2477–2482, 1993.

18. Leadbetter and Greenberg, "Metabolism of acyl-homoserine lactone quorum sensing signals by *Variovorax paradoxus*," *J. Bacteriol.* 182: 6921–6926, 2000.

19. Lewenza et al., "Quorum sensing in *Burkholderia cepacia*: identification of the LuxRI homologs CepRI," *J. Bacteriol.* 181: 748–756, 1999.

20. Matsuda and Komatsu, "Molecular cloning and structure of the gene for 7β-(4-carboxybutanamido) cephalosporadic acid acylase from a *Pseudomonas* strain," *J. Bacteriol.* 163: 1222–1228, 1985.

21. Matsuda et al., "Nucleotide sequence of the genes for two distinct cephalosporin acylases from a *Pseudomonas* strain," *J. Bacteriol.* 169: 5821–5826, 1987.

22. Nasser et al., "Characterization of the *Erwinia chrysanthemi* expI-expR locus directing the synthesis of two N-acyl-homoserine lactone signal molecules," *Mol. Microbiol.* 29: 1391–1405, 1998.

23. Passador et al., "Expression of *Pseudomonas aeruginosa* virulence genes requires cell-to-cell communication," *Science* 260: 1127–1130, 1993.

24. Pearson et al., "Structure of the autoinducer required for expression of *Pseudomonas aeruginosa* virulence genes," *Proc. Natl. Acad. Sci. USA* 91: 197–201, 1994

25. Piper et al., "Conjugation factor of *Agrobacterium tumefaciens* regulates Ti plasmid transfer by autoinduction," *Nature* 362: 448–450, 1993.

26. Pirhonen et al., "A small diffusible signal molecule is responsible for the global control of virulence and exoenzyme production in the plant pathogen *Erwinia carotovora*," *EMBO J.* 12: 2467–2476, 1993.

27. Schumacher et al., "Penicillin acylase from *E. coli*: unique gene-protein relation," *Nucleic Acids Res.* 14: 5713–5727, 1986.

28. Staskawicz et al., "Molecular characterization of cloned avirulence genes from race 0 and race 1 of *Pseudomonas syringae* pv. *glycinea*," *J. Bacteriol.* 169: 5789–5794, 1987.

29. Takeshima et al., "A deacylation enzyme for aculeacin A, a neutral lipopeptide antibiotic, from *Actinoplanes utahensis*: purification and characterization," *J. Biochem.* 105: 606–610, 1989.

30. Verhaert et al., "Molecular cloning and analysis of the gene encoding the thermostable penicillin G acylase from *Alcaligenes faecalis*," *Appl. Env. Microbiol.* 63: 3412–3418, 1997.

31. Zhang et al., "*Agrobacterium* conjugation and gene regulation by N-acyl-L-homoserine lactones," *Nature* 362: 446–447, 1993.

The following examples are provided to illustrate the invention described herein and should not be construed to limit the appended claims.

EXAMPLES

Example 1

Bacterial Isolation

A bacterial biofilm sample was collected from a water treatment system and screened to isolate AHL inactivation bacterial strains. The bacterial mixture was suspended in sterilized water with shaking for 1 hour before spreading onto YEB medium (yeast extract, 5 g/l; casein hydrolysate, 10 g/l; NaCl, 5 g/l; sucrose, 5 g/l; $MgSO_4 7H_2O$, 0.5 g/l and agar, 15 g/l) plates. Individual colonies were restreaked on new plates to ensure purity of the isolates. Bacterial isolates were cultured in LB medium (tryptone, 10 g/L; yeast extract, 5 g/L, and NaCl, 10 g/L; pH7.0) in 1.5-ml Eppendorf™ tubes or 96-well plates at 28° C., with shaking, overnight, and assayed for AHL inactivation activity.

Example 2

AHL Inactivation Bioassay

The bacterial culture to be assayed was mixed with an equal volume of fresh medium containing 20 μM N-β-oxooctanoyl-L-homoserine lactone (OOHL), or another AHL, when specified, to form a reaction mixture. The reaction mixture was incubated at 28° C. for 4 to 5 hours, followed by 30 minute sterilization under UV light. Plates containing 20 ml MM agar medium ($K_2HPO_{41}$ 10.5 g/L; $KH_2PO_4$, 4.5 g/L; $MgSO_4.7H_2O$, 0.2 g/L; $FeSO_4$, 4.5 mg/L; $CaCl_2$; 10 mg/L; $MnCl_2$, 2 mg/L; $(NH_4)_2SO_4$, 2.0 g/L; mannitol, 2.0 g/L; pH 7.0) supplemented with 5-bromo-4-chloro-3-indolyl β-D-galactopyranoside (X-Gal, 40 μg/ml) were prepared. The solidified medium was cut, still inside the plate, into separated slices (approximately 1 cm in width). See FIG. 1. Five microliters of sterilized reaction mixture was loaded at the top of an MM agar strip, and then AHL indicator cells (*Agrobacterium tumefaciens* strain NT1 (traR; tra:lacZ749) (25) 0.7 μl cell suspension with an optical density at 600 nm of 0.4) were spotted at progressively further distances from the loaded samples. Plates were incubated at 28° C. for 24 hours. A positive result for AHL inactivation is shown by the absence of blue colonies on the slice. A negative result for AHL inactivation is shown by the presence of blue colonies on the slice. For assay of protein for enzyme activity, total soluble bacterial protein was incubated with 20 μM of OOHL (or other AHL) at 37° C. for 1 hour as the reaction mixture.

Example 3

Identification and Cloning the qsbA Gene

Two bacterial isolates from the biofilm sample with distinct phenotypes, XJ12B and XJ12A, were found to possess the ability to inactivate AHL, with XJ12B showing stronger enzyme activity. The XJ12B late was cultured, centrifuged and sonicated. The strongest enzymatic activity was associated with the cell debris fraction rather than the soluble protein and supernatant fractions. These results indicated that the AHL inactivation activity is membrane associated. Sequencing of 16S rRNA was performed to identify the XJ12A and XJ12B lates. The 16S rRNA sequences of these isolates showed 97% and 96% identity, respectively, with that of *Ralstonia eutropha*.

To identify the gene encoding for AHL inactivation, a cosmid library of 1600 clones was constructed in *E. coli* with the genomic DNA of *Ralstonia* sp. strain XJ12B. Genomic DNA from the isolated *Ralstonia* sp. strain XJ12B was partially digested with Sau3A. The resulting DNA fragments were ligated to the dephosphorylated BamH1 site of cosmid vector pLAFR3 (28). The ligated DNA was packed with Gigapack IIIXL Packaging Extract (Stratagene) and transfected into *E. coli* DH5alpha. These *E. coli* transfectants were screened for AHL inactivation activity according to the methods described in Example 2 using OOHL as the substrate. Only a single clone (p13H10) was identified as showing AHL inactivation activity (see FIG. 1A, slice 1). To subclone the gene encoding the detected activity, cosmid DNA from the positive clone p13H10 was partially digested with Sau3A and fused into BamH1 digested cloning vector pGEM-3Zf (+). The plasmids were ligated and transformed into *E. coli*, and the *E. coli* were assayed for the ability to inactivate AHL as described in Example 2. Clone p2B10, which contains a 4 kb insert, had AHL inactivation activity (see FIG. 1A, slice 2). The TGS™ Template Generation System F-700 (Finnzymes OY) was used to mutate p2B10 plasmid DNA by randomly inserting the artificial Mu transposon, following the manufacturer's instructions. Plasmid clone p2B10, which contains the 4 kb insert containing the qsbA gene, was used as a template. Fifteen mutant clones were produced, and none was able to inactive AHL. Bacterial cultures of *E. coli* DH5α containing pMUG3 and pMUC6 are shown as examples in FIG. 1A, slices 3 and 4, respectively. Plasmids were subsequently purified for sequencing using primers supplied in the kit.

Example 4

Sequencing and Sequence Analysis of the qsbA Gene

Sequencing was performed according to known methods using ABI Prism dRhodamine Terminator Cycle Sequencing Ready Reaction Kit (Perkin-Elmer Applied Biosystems). The 4 kb fragment from clone p2B10 was completely sequenced and is shown in Table I. The sequence contains an open reading frame of 2385 nucleotides with an ATG start codon and a TGA stop codon (SEQ ID NO: 1, nucleotides 1259–3643). Based on the MU transposon mutagenesis data described in Example 3, this open reading frame is the coding region of the AHL inactivation gene, designated as qsbA. A putative ribosome binding site (AGGAGA) is located 6 base pairs upstream of the first ATG start codon (underlined in Table I).

The deduced peptide sequence shows the typical polypeptide primary structure of aculeacin A acylases (AACs) and penicillin G acylases, with signal peptide-α subunit-spacer-β subunit organization (16, 30). There are four additional potential start codons located 3, 36, 189 and 384 downstream from the first ATG. The longest open reading frame encodes 794 amino acids, with a predicted molecular weight of 85373 Daltons. The deduced peptide has 78 strongly basic and strong acid amino acid residues and a predicted isoelectric point of 7.48. The first 20 amino acid residues of the assumed open reading frame appear to be a signal peptide.

The peptide sequence of qsbA deduced from the open reading frame shares 40–52% identity with AACs from *Deinococcus radiodurans* strain R1, *Actinoplanes utahensis* and a putative acylase from *Pseudomonas aeruginosa*, The AACs' catalyze deacylation of their substrates. These AAC genes are translated as single precursor polypeptide and then processed to the active form of two subunits. By alignment with the peptide sequences from *D. radiodurans* strain R1, *A. utahensis* and *P. aeruginosa*, Table II, the presumed α and β subunits are located at amino acid positions 36–217 and 233–794, respectively, with a 15 amino acid spacer between them. QsbA shares less than 28% homology with penicillin G acylase (20) and cephalosporin acylase (21). See Table II. The amino acid sequence alignment in Table II was analyzed by the Clustal W program available from the European Bioinformatics Institute website (http://www.ebi.ac.uk).

Example 5

Expression of the QsbA Gene

The coding region of the qsbA gene was amplified by PCR using a forward primer 5'-CGT GGATCCATGATGCAGGATTCGCCGCTGCGC-3' (SEQ ID NO: 6) and a reverse primer 5'-CGC GAATTCACCGGCAGCCCTCATGCGACAAC-3' (SEQ ID NO: 7) containing BamH1 and EcoR1 restriction sites, respectively. The amplified PCR products were digested using the above restriction enzymes and fused in-frame to the coding sequence of the glutathione S-transferase (GST) gene under the control of the isopropyl β-D-thiogalactopyranoside (IPTG) inducible lac promotor in vector pGEX-2T (Amersham Pharmacia) to generate construct pGST-QsbA. pGST-QsbA was transformed into *E. coli* and expressed.

Total soluble protein was extracted from the recombinant *E. coli* cells harboring the GST-QsbA-encoding fusion construct according to methods known in the art, based on the methods described in Dong et al. (9), and assayed for AHL inactivation. The total soluble protein from *E. coli* containing GST vector only was used as a control. For the bioassay, 50 μl of the soluble protein preparation (20 μg/μl) was added to the same volume of 40 μM AHL, e.g., OOHL. After a 1 hour incubation at 37° C., the reaction mixture was assayed as described in Example 2. Representative data, shown in FIG. 1B, slice 1, indicate that the soluble GST-QsbA fusion protein effectively eliminated OOHL activity.

Example 6

Characterization of the Substrate Spectrum of GST-QsbA Fusion Protein Expressed in *E. coli*

To determinate the substrate spectrum of QsbA, total soluble protein extracted from the recombinant *E. coli* (pGST-QsbA) was assayed for inactivation of AHLs with acyl chains of differing lengths according to the methods of Example 2. The following AHLs were synthesized according to known methods as described by Zhang et al. (31): (1) N-octanoyl-L-homoserine lactone (C8HSL, OOHL); (2) N-decanoyl-L-homoserine lactone (C1DHSL, DHL); (3) N-β-oxohexanoyl-L-homoserine lactone (3-oxo-C6HSL, OHHL); (4) N-β-oxohexanoyl-L-homoserine lactone (3-oxo-C12HSL, OdDHL); (5) N-β-oxohexanoyl-L-homoserine lactone (3-oxo-C8HSL, OOHL). The butyl and hexyl esters of N-β-oxohexanoyl-L-homoserine were prepared by esterification of N-β-oxohexanoyl-L-homoserine lactone with 1-butanol and 1-hexanol respectively, in the presence of small amount of Dowex 50H+ resin (Aldrich). The reaction was conducted at 60° C. for 2 hours and the products were purified by silica column chromatography.

QsbA completely inactivated OOHL, N-β-oxodecanoyl-L-homoserine (ODHL) and N-β-oxododecanoyl-L-homoserine (OdDHL), which have acyl chains of 8, 10 and 12 carbons, respectively, at the concentrations tested (data not shown). QsbA also strongly inactivated N-β-octanoyl-L-homoserine (OHL) and N-β-decanoyl-L-homoserine (DHL), which have acyl chains of 8 and 10 carbons, respectively (data not shown). However, under the same reaction conditions, QsbA had less inactivating activity for N-β-oxohexanoyl-L-homoserine (OHHL), which has an acyl chain of 6 carbons (data not shown). The total soluble protein extract from control E. coli (pGST) did not show any activity against AHLs (data not shown).

QsbA also completely inactivated the butyl and hexyl esters of N-β-octanoyl-L-homoserine (data not shown). These two esters of N-β-octanoyl-L-homoserine showed comparable induction activity with OOHL when assayed with the AHL reporter strain A. tumefaciens NT1 (traR; tra:lacZ749) (data not shown). AHL-lactonase (encoded by aiiA) did not inactivate these substrates. These substrate specificity data are consistent with identification of QsbA as an AHL-acylase.

Example 7

Purification of AHL-Acylase Encoded by the qsbA Gene

The GST-[AHL-acylase] fusion protein was purified using a glutathione Sepharose 4B affinity column following the manufacturer's instructions (Pharmacia). AHL-acylase was cleaved by digestion with thrombin (Sigma). Protein concentration was determined by measuring $OD_{280}$.

Figure 2A:
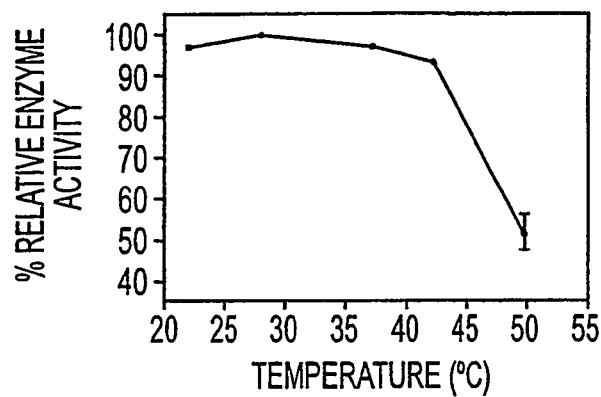
FIG. 2 is a graph showing the temperature and pH optimum profiles of AHL acylase.
Figure 2B:
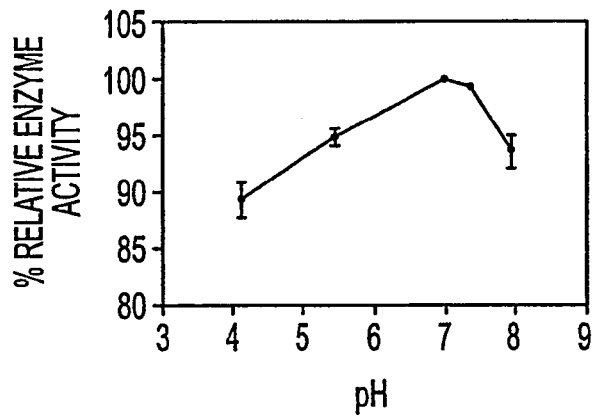
Figure 3:
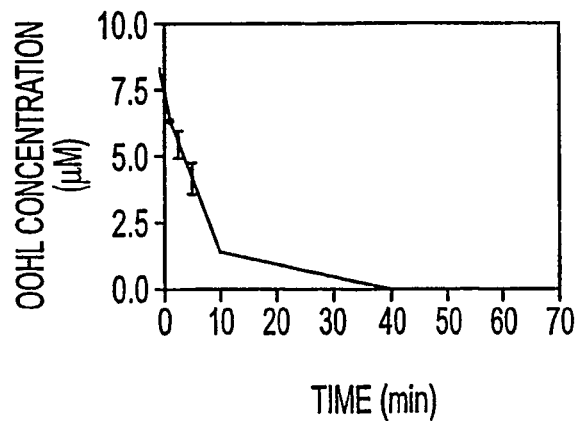
FIG. 3 is a graph showing the time course of OOHL inactivation by the purified AHL-acylase.

The purified AHL-acylase was incubated with OOHL for 20 minutes and the relative enzyme activity was measured by determining the residual OOHL in the reaction mixture, which contained 8μM OOHL and about 0.6 μg AHL-acylase in a total reaction volume of 50 ml 1×PBS buffer. The reactions were stopped by addition of 1% SDS before loading on the assay plate. Determination of the OOHL activity was carried out in quadruplicate. AHL-acylase degraded OOHL in a range of temperatures from 22–42° C. at pH 7.0. See FIG. 2. The optimal temperature for enzyme activity was found to be approximately 28° C. Reaction temperature higher than 42° C. decreased enzyme activity sharply. The optimal pH for enzyme activity also was determined. The AHL-acylase has a relatively narrow optimal pH range from pH 6.5 to 7.5. See FIG. 2. The time course of OOHL inactivation by the purified AHL-acylase was determined at 30° C. See FIG. 3. After 10 minutes, more than 82% OOHL had been degraded; the reaction rate was estimated to be about 55 pmols per μg AHL-acylase per minute.

What is claimed is:

1. A composition of matter which comprises an isolated peptidic sequence according to SEQ ID NO: 2.

2. A composition of matter which comprises an isolated peptidic sequence which is amino acids 36–217 of SEQ ID NO: 2.

3. A composition of matter which comprises an isolated peptidic sequence which is amino acids 233–794 of SEQ ID NO: 2.

4. An isolated peptide of SEQ ID NO:2.

5. An isolated peptide which is amino acids 36–217 of SEQ ID NO:2.

6. An isolated peptide which is amino acids 233–794 of SEQ ID NO:2.

* * * * *